US012662504B2

(12) United States Patent
Urai et al.

(10) Patent No.: US 12,662,504 B2
(45) Date of Patent: Jun. 23, 2026

(54) HIGH-SOLUBILITY REBAUDIOSIDE D COMPLEX

(71) Applicant: SUNTORY HOLDINGS LIMITED, Osaka (JP)

(72) Inventors: Soichiro Urai, Kanagawa (JP); Koji Nagao, Kanagawa (JP); Yoshiaki Yokoo, Kanagawa (JP); Hiroshi Takiyama, Tokyo (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 931 days.

(21) Appl. No.: 17/788,906

(22) PCT Filed: Dec. 25, 2020

(86) PCT No.: PCT/JP2020/048740
§ 371 (c)(1),
(2) Date: Jun. 24, 2022

(87) PCT Pub. No.: WO2021/132567
PCT Pub. Date: Jul. 1, 2021

(65) Prior Publication Data
US 2023/0059067 A1     Feb. 23, 2023

(30) Foreign Application Priority Data
Dec. 27, 2019    (JP) ................................ 2019-238753

(51) Int. Cl.
*C07H 15/24* (2006.01)
*A23L 2/60* (2006.01)
*A23L 27/30* (2016.01)

(52) U.S. Cl.
CPC ................ *C07H 15/24* (2013.01); *A23L 2/60* (2013.01); *A23L 27/31* (2016.08); *A23L 27/36* (2016.08)

(58) Field of Classification Search
CPC ............. A23L 2/60; A23L 27/36; A23L 27/34
See application file for complete search history.

(56) References Cited

U.S. PATENT DOCUMENTS

| | | |
|---|---|---|
| 2008/0226773 A1 | 9/2008 | Lee |
| 2008/0226804 A1 | 9/2008 | Talebi et al. |
| 2009/0104326 A1 | 4/2009 | Catani et al. |
| 2012/0164083 A1 | 6/2012 | Palmer et al. |
| 2013/0251881 A1 | 9/2013 | Mutilangi et al. |
| 2013/0274351 A1 | 10/2013 | Markosyan et al. |
| 2014/0342043 A1 | 11/2014 | Bell et al. |
| 2014/0342044 A1 | 11/2014 | Bell et al. |
| 2015/0030547 A1 | 1/2015 | Liao et al. |
| 2016/0255868 A1 | 9/2016 | Panarisi et al. |
| 2016/0271155 A1 | 9/2016 | Liu et al. |
| 2018/0289042 A1 | 10/2018 | Bell et al. |
| 2019/0077823 A1 | 3/2019 | Markosyan |

FOREIGN PATENT DOCUMENTS

| | | | |
|---|---|---|---|
| CN | 101662944 A | 3/2010 | |
| CN | 101662954 A | 3/2010 | |
| CN | 102573521 A | 7/2012 | |
| CN | 105047738 A | 3/2016 | |
| EP | 3181574 A1 | 12/2011 | |
| EP | 2651960 A2 | 10/2013 | |
| JP | 2009-517021 A | 4/2009 | |
| JP | 2010-527609 A | 8/2010 | |
| JP | 2011-529688 A | 12/2011 | |
| JP | 2013-518118 A | 5/2013 | |
| JP | 2015-511498 A | 4/2015 | |
| JP | 2016-518143 A | 6/2016 | |
| JP | 2016-521974 A | 7/2016 | |
| JP | 2017-519812 A | 7/2017 | |
| WO | 2007/061757 A1 | 5/2007 | |
| WO | 2008/112857 A1 | 9/2008 | |
| WO | 2008/112966 A1 | 9/2008 | |
| WO | 2008/147723 A1 | 12/2008 | |
| WO | 2010/014813 A2 | 2/2010 | |
| WO | 2010/042093 A2 | 4/2010 | |
| WO | 2011/028671 A1 | 3/2011 | |
| WO | 2011/046423 A1 | 4/2011 | |
| WO | 2011/094423 A1 | 8/2011 | |
| WO | WO-2012082587 A2 * | 6/2012 | ............. A23L 27/34 |
| WO | 2013/148177 A1 | 10/2013 | |
| WO | 2014/098833 A1 | 6/2014 | |
| WO | 2015/012987 A1 | 1/2015 | |
| WO | 2015/077509 A1 | 5/2015 | |
| WO | 2015/077511 A1 | 5/2015 | |
| WO | 2015/171555 A1 | 11/2015 | |
| WO | 2016/141152 A1 | 9/2016 | |

OTHER PUBLICATIONS

Upreti, Int. J. Mol. Sci. 2011, 12, 7529-7553. (Year: 2011).*
International Search Report issued in PCT/JP2020/048740, dated Mar. 2, 2021, along with an English language translation.
Extended European Search Report issued on Dec. 18, 2023 in European patent application No. 20904574.9.
Office Action issued on Jul. 5, 2023 in Chinese patent application No. 202080089964.1.

* cited by examiner

*Primary Examiner* — Layla D Berry
(74) *Attorney, Agent, or Firm* — GREENBLUM & BERNSTEIN, P.L.C.

(57) ABSTRACT

The present invention pertains to a novel complex of rebaudioside D having increased water-solubility, and a novel method for increasing the solubility of rebaudioside D in water. The present invention provides a complex containing Reb. D and one or more compounds selected from sugars as well as water-soluble vitamins and salts thereof, wherein the water-solubility of Reb. D at a water temperature of 25° C. is 75 mg/100 g-H₂O or higher.

10 Claims, 11 Drawing Sheets

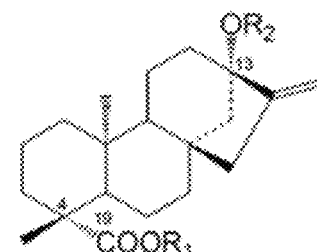

| Name | R₁ | R₂ |
|---|---|---|
| Steviol | H | H |
| Steviolmonoside | H | Glc |
| Steviolbioside | H | Glc-Glc(β2→1) |
| Dulcoside A | Glc | Glc-Rha(β2→1) |
| Rubusoside | Glc | Glc |
| Stevioside | Glc | Glc-Glc(β2→1) |
| Rebaudioside A | Glc | Glc-Glc(β2→1)<br>Glc(β3→1) |
| Rebaudioside B | H | Glc-Glc(β2→1)<br>Glc(β3→1) |
| Rebaudioside C (Dulcoside B) | Glc | Glc-Rha(β2→1)<br>Glc(β3→1) |
| Rebaudioside D | Glc-Glc(β2→1) | Glc-Glc(β2→1)<br>Glc(β3→1) |
| Rebaudioside E | Glc-Glc(β2→1) | Glc-Glc(β2→1) |
| Rebaudioside F | Glc | Glc-Xyl(β2→1)<br>Glc(β3→1) |

Figure 1

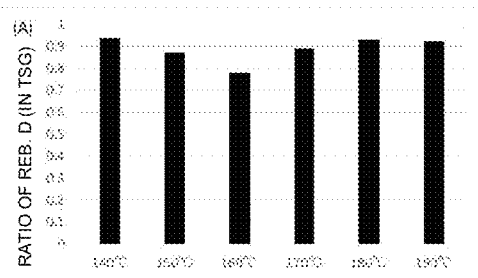
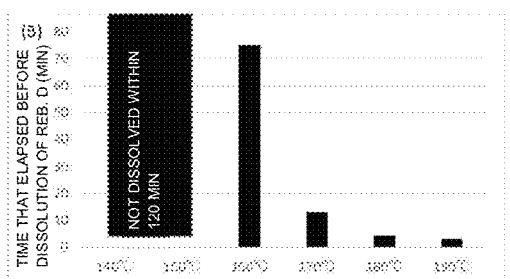
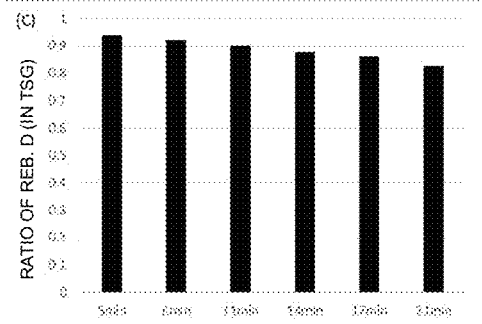
Figure 6
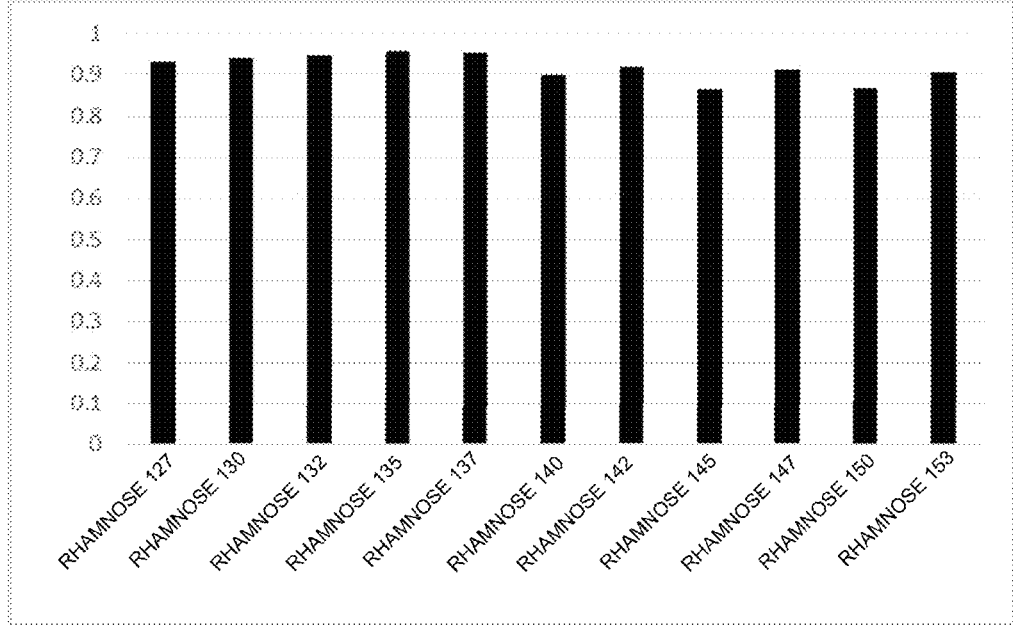
Figure 7

(A)
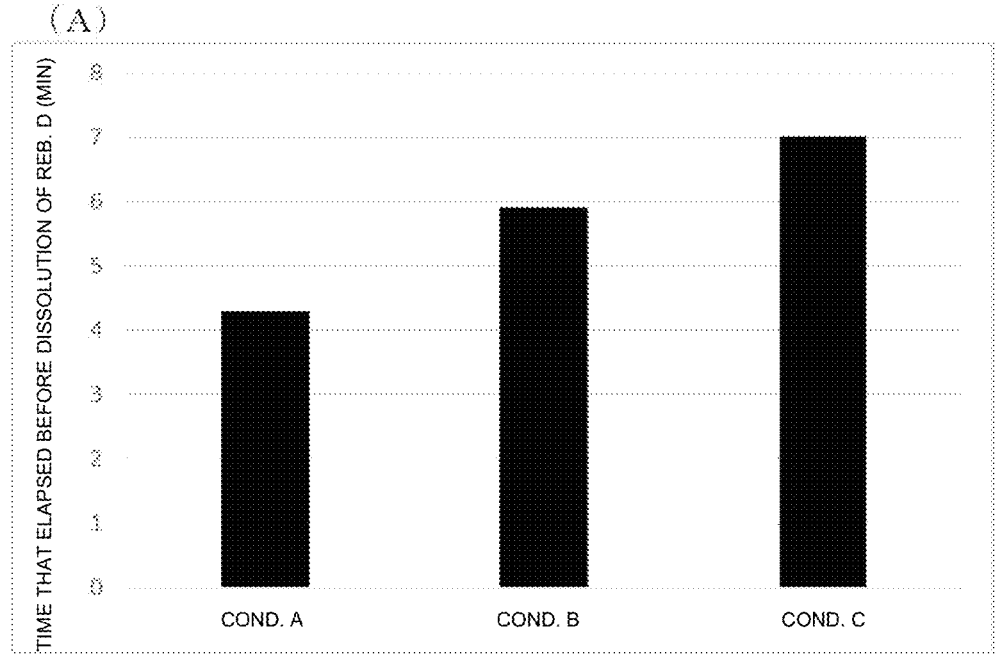
(B)
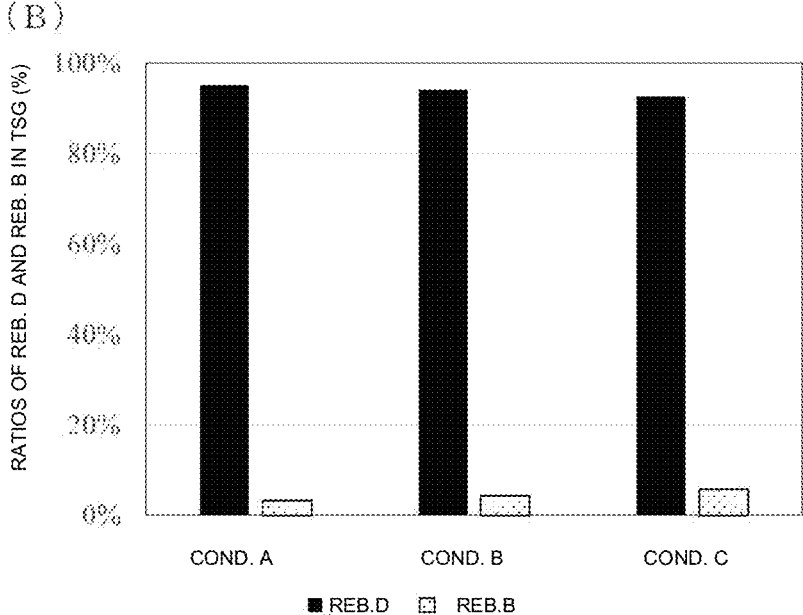
Figure 12

HIGH-SOLUBILITY REBAUDIOSIDE D COMPLEX

TECHNICAL FIELD

The present invention relates to a high-solubility rebaudioside D complex and a method for producing the same. The present invention further relates to a sweetener composition containing the high-solubility rebaudioside D complex and a food or beverage containing the complex or the sweetener composition.

BACKGROUND ART

Leaves of *Stevia rebaudiana* contain a secondary metabolite called Steviol which is one type of diterpenoids, where a steviol glycoside provides sweetness that is nearly 300 times the sweetness of sugar and is therefore utilized as a calorieless sweetener in the food industry. The demand for calorieless sweeteners is growing day by day as obesity has become a serious social problem worldwide and also for the sake of health promotion and reduction in the medical expenditure. Currently, aspartame and acesulfame potassium, which are artificially synthesized amino acid derivatives, are utilized as artificial sweeteners, but natural calorieless sweeteners like steviol glycosides are expected to be safer and more likely to gain public acceptance.

The structure of general steviol glycosides is shown in FIG. 1. The major steviol glycosides of *stevia* include a glycoside called rebaudioside A (Reb. A) that has four sugar moieties. The amount of Stevioside, namely, a tri-glycosylated steviol glycoside that is a precursor thereof is the largest, and these two glycosides are the main substances for the sweetness of *stevia*. Stevioside accounts for the largest content in *stevia* leaves and is known to provide sweetness that is about 250 to 300 times the sweetness of sugar. Reb. A is a tetra-glycosylated steviol glycoside that has strong sweetness (200 to 450 times that of sugar) with good taste quality. They have been drawing attention as calorieless sweeteners.

As a steviol glycoside whose taste quality is superior to that of Reb. A, rebaudioside D (Reb. D) has been drawing attention. Reb. D has a structure in which five sugar moieties are added to the diterpene skeleton shown in FIG. 1 and provides sweetness that is about 200 to 300 times the sweetness of sugar. Accordingly, attempts have been made to add rebaudioside D to beverages as a sweetener (for example, Patent Literatures 1 and 2).

However, the water solubility of rebaudioside D is lower than those of rebaudioside A and the like. For this reason, attempts have been made to improve the water solubility of rebaudioside D. For example, in Patent Literature 3, attempts were made to improve the solubility of rebaudioside D in an aqueous solution by mixing rebaudioside D with a solubilization improver and a stabilizer in water, followed by spray drying. Further, in Patent Literature 4, attempts were made to obtain a steviol glycoside composition having improved solubility by adding water and ethanol to a steviol glycoside composition containing rebaudioside D; mixing, heating and then cooling the mixture; separating a solid phase from the obtained colloidal suspension; and drying the separated solid phase.

CITATION LIST

Patent Literature

Patent Literature 1: Japanese National-phase PCT Laid-Open Patent Publication No. 2016-518143
Patent Literature 2: Japanese National-phase PCT Laid-Open Patent Publication No. 2016-521974
Patent Literature 3: Japanese National-phase PCT Laid-Open Patent Publication No. 2015-511498
Patent Literature 4: US Laid-Open Publication No. 2019/0077823

SUMMARY OF INVENTION

Technical Problem

Under the above-described circumstances, currently, it has been desired to develop a novel complex of rebaudioside D having increased water solubility and a novel method for increasing the solubility of rebaudioside D in water.

Solution to Problem

The present inventors comprehended that, by forming a complex of rebaudioside D and at least one compound selected from carbohydrates and water-soluble vitamins and salts thereof, a novel complex of rebaudioside D having increased water solubility can be obtained. The present invention is based on this finding.

The present invention includes inventions of the below-described embodiments.

[1] A complex comprising:
   Reb. D; and
   at least one compound selected from carbohydrates and water-soluble vitamins and salts thereof,
   wherein the water solubility of Reb. D at a water temperature of 25° C. is 75 mg/100 g-$H_2O$ or higher.

[2] The complex according to [1], wherein the Reb. D is amorphous.

[3] The complex according to [1], wherein the complex comprises a eutectic crystal.

[4] The complex according to any one of [1] to [3], wherein the complex consists essentially of:
   Reb. D; and
   at least one compound selected from carbohydrates and water-soluble vitamins and salts thereof.

[5] The complex according to any one of [1] to [4], wherein the at least one compound selected from the carbohydrates and the water-soluble vitamins and the salts thereof is selected from sugars or sugar alcohols.

[6] The complex according to any one of [1] to [5], wherein the at least one compound selected from the carbohydrates and the water-soluble vitamins and the salts thereof comprises at least one selected from sucrose, fructose, maltose, xylitol, erythritol, maltitol, palatinose, mannose, arabinose, lactitol, glucose, allulose, xylose, rhamnose and ribose.

[7] The complex according to [5], wherein the sugar alcohols comprise at least one selected from erythritol, sorbitol, xylitol, maltitol, isomaltitol, lactitol, maltotriitol, isomaltotriitol and panitol.

[8] The complex according to [5], wherein the sugars comprise at least one selected from glucose, rhamnose, xylose, ribose, allulose, arabinose, mannose, fructose, sucrose, maltose and lactose.

[9] The complex according to any one of [1] to [8], wherein the content of Reb. D is an amount equal to or less than the saturation solubility relative to the at least one compound selected from the carbohydrates and the water-soluble vitamins and the salts thereof.

[10] The complex according to any one of [1] to [9], wherein the compound is erythritol, and wherein the complex has a peak at at least one selected from $2\theta=14.8\pm0.2$ deg, $20.2\pm0.2$ deg, $24.5\pm0.2$ deg and $27.9\pm0.2$ deg in X-ray diffraction (CuKα: λ=1.5405 Å).

[10-1] The complex according to any one of [1] to [10], wherein the content of Reb. D is 10 to 300 mg relative to 1 g of the at least one compound selected from the carbohydrates and the water-soluble vitamins and the salts thereof.

[10-2] The complex according to any one of [1] to [10-1], wherein the complex comprises Reb. D and erythritol, wherein the content of Reb. D is 10 to 300 mg relative to 1 g of erythritol.

[10-3] The complex according to any one of [1] to [10-2], wherein the complex comprises Reb. D, erythritol and fructose, wherein the content of Reb. D is 10 to 300 mg relative to 1 g of the total of erythritol and fructose.

[11] A sweetener composition comprising the complex according to any one of [1] to [10].

[11-1] A sweetener composition comprising the complex according to any one of [1] to [10-3].

[12] The sweetener composition according to [11] or [11-1], further comprising at least one selected from the group consisting of Reb. A, Reb. B, Reb. C, Reb. E, Reb. F, Reb. G, Reb. I, Reb. J, Reb. K, Reb. M, Reb. N, Reb. O, Reb. Q, Reb. R, Reb. V, Reb. W, Reb. KA, dulcoside A, rubusoside, steviol, steviolmonoside, steviolbioside, stevioside, sucrose, high fructose corn syrup, erythritol, Mogroside V, corn syrup, aspartame, sucralose, acesulfame potassium, saccharin and xylitol.

[13] A food or beverage comprising the complex according to any one of [1] to [10] or the sweetener composition according to item [11] or [12].

[13-1] A food or beverage comprising the complex according to any one of [1] to [10-3] or the sweetener composition according to [11], [11-1] or [12].

[14] A method for producing a complex comprising:
    Reb. D; and
    at least one compound selected from carbohydrates and water-soluble vitamins and salts thereof, wherein the method comprises:
    heating at least one compound selected from carbohydrates and water-soluble vitamins and salts thereof to form a melt;
    dissolving Reb. D in the melt; and
    cooling the melt in which Reb. D is dissolved.

[15] The method according to [14], wherein the method comprises forming the melt at a temperature lower than the decomposition point of Reb. D.

[16] The method according to [14] or [15], wherein the cooling is performed at a temperature equal to or lower than the nucleation temperature of the compound constituting the melt.

[17] The method according to any one of [14] to [16], wherein:
    erythritol is used as the at least one compound selected from the carbohydrates and the water-soluble vitamins and the salts thereof; and
    the cooling is performed in a manner such that the solidification of erythritol starts at a temperature of 120° C. or lower.

[18] The method according to any one of [14] to [17], wherein the cooling is performed by cooling by stirring or static cooling.

Advantageous Effects of Invention

According to the present invention, a novel complex of rebaudioside D having increased water solubility and a method for producing the same can be provided.

BRIEF DESCRIPTION OF DRAWINGS

FIG. 1 shows the structure and names of general steviol glycosides.

FIG. 6 shows the composition ratio of Reb. D, etc. of each sample obtained by melting erythritol at each of different melting temperatures and dissolving Reb. D therein in Example F. FIG. 6(A) shows the composition ratio of Reb. D in the solution of the complex obtained at each temperature. FIG. 6(B) shows the time that elapsed before dissolution of Reb. D in erythritol melted at each temperature. FIG. 6(C) shows the ratio of Reb. D in TSG contained in each sample obtained with each dissolution time when dissolving Reb. D at 170° C.

FIG. 7 shows the ratio of Reb. D in TSG contained in each sample obtained by melting rhamnose at each of different melting temperatures and dissolving Reb. D therein in Example G.

FIG. 12 shows the concentration of Reb. D (dissolution amount of Reb. D) obtained when each complex obtained by changing the addition order of raw materials was dissolved in water in Example L. (A) shows the time that elapsed before Reb. D in each complex obtained under each condition was dissolved in water, and (B) shows the ratios of Reb. D and Reb. B to the total steviol glycoside (TSG) under each condition.

FIG. 13(A) shows the concentration of Reb. D (dissolution amount of Reb. D) obtained when dissolving each complex in water, and FIG. 13(B) shows the temperature change of each sample at the time of cooling.

FIG. 15(A) shows the temperature change of each sample at the time of cooling, and FIG. 15(B) shows the dissolution amount Reb. D obtained when dissolving each complex in water.

DESCRIPTION OF EMBODIMENTS

Figure 2:
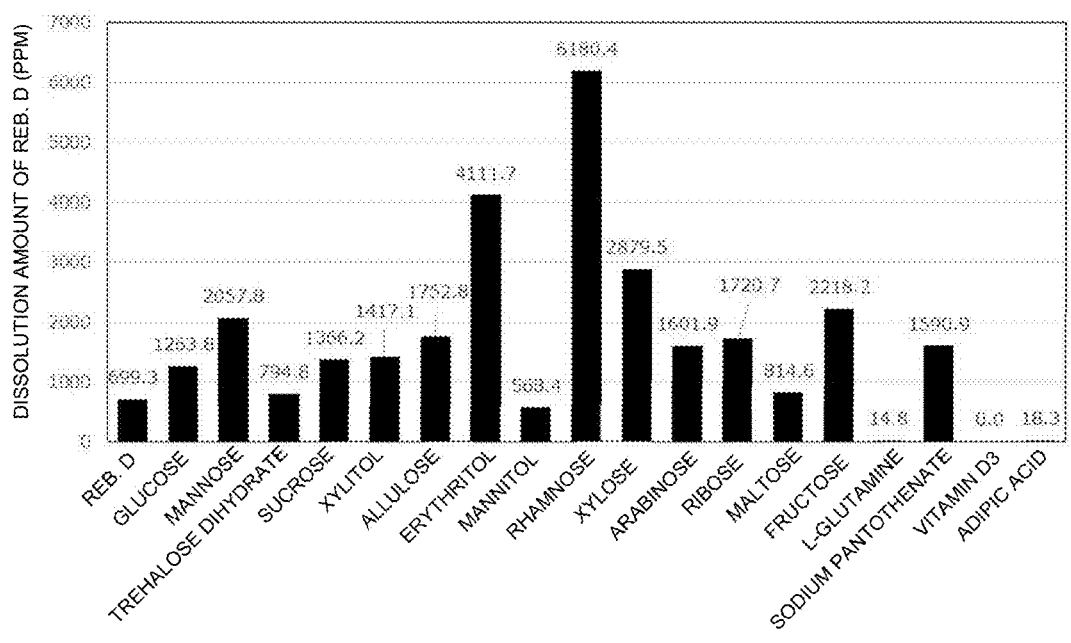
FIG. 2 shows the results of evaluation of solubility in Example B.

Hereinafter, the present invention will be described in detail. The below-described embodiments are provided only for illustrative purposes, and it is not intended that the present invention be limited only to these embodiments. The present invention can be practiced employing various modes without departing from the gist of the present invention. Note that all the documents, laid-open publications, patents and other patent documents cited in this specification are incorporated herein by reference. Further, the contents disclosed in the specification and drawings of Japanese Patent Application No. 2019-238753 filed on Dec. 27, 2019, to which priority is claimed by the present application, are incorporated herein.

As used herein, all of "Rebaudioside", "Reb" and "Reb." represent the same meaning, that is "rebaudioside". Similarly, as used herein, "dulcoside" means "dulcoside". As used herein, "TSG" means "total steviol glycoside", and means Reb. A, Reb. B, Reb. C, Reb. D, Reb. F, Reb. M, stevioside, Reb. N, Reb. O, Reb. I, steviolbioside, dulcoside A, Reb. E, Reb G and rubusoside, or the total amount thereof.

As used herein, "ppm" means "mass ppm" unless otherwise stated. In this specification, when the amount of Reb. D dissolved in water is 10 mass ppm, the water solubility of Reb. D is 1 mg/100 g-$H_2O$. Further, since the specific gravity of a beverage is usually 1, "mass ppm" can be equated with "mg/L". Further, in this specification, the wording "about" means that the subject exists within a range of the numerical value following "about" ±25%, ±10%, ±5%, ±3%, ±2% or ±1%. For example, "about 10" means a range of from 7.5 to 12.5.

1. Complex Containing Reb. D

As described above, the present inventors comprehended that, by forming a complex of rebaudioside D and at least one compound selected from carbohydrates and water-soluble vitamins and salts thereof, a novel complex of rebaudioside D having increased water solubility can be obtained. Accordingly, the complex of the present invention is a complex containing Reb. D and at least one compound selected from carbohydrates and water-soluble vitamins and salts thereof (hereinafter also referred to as "the complex of the present invention"). In an embodiment of the present invention, the water solubility of Reb. D in the complex of the present invention at a water temperature of 25° C. is 75 mg/100 g-$H_2O$ or higher. In this specification, the "complex" means a substance in which two or more components are combined and integrated. Examples of the complex include a two-component complex obtained by melting one component and dissolving the other component therein, followed by solidifying it. In an embodiment of the present invention, the complex of the present invention has a satisfactory taste quality. The complex in a preferred embodiment of the present invention has a taste quality equal to or higher than that of Reb. D alone, and for example, it is excellent with respect to lingering sweet aftertaste.

Rebaudioside D (Reb. D) contained in the complex of the present invention has a structure in which 5 sugars are added to the diterpene skeleton shown in FIG. 1 as described above, and specifically, it is represented by the following chemical formula.

Reb. D has a very high sweetness (about 200 to 300 times that of sugar), and is superior in terms of an aftertaste and the like to Reb. A that is generally distributed. Meanwhile, the water solubility of Reb. A at a water temperature of 7.5° C. is about 2,000 to 4,000 mg/100 g-$H_2O$, whereas the water solubility of Reb. D that is currently commercially available at a water temperature of 7.5° C. is about 40 to 50 mg/100 g-$H_2O$. For this reason, though Reb. D has a more preferable taste quality when compared to Reb. A, it is difficult to add Reb. D to a food or beverage in an amount sufficient for imparting sweetness thereto.

According to the present invention, by forming a complex of Reb. D and at least one compound selected from carbohydrates and water-soluble vitamins and salts thereof, the water solubility of Reb. D in the complex can be improved. Specifically, by using the complex according to an embodiment of the present invention, Reb. D can be dissolved in water with a solubility of higher than 40 to 50 mg/100 g-$H_2O$ at a water temperature of 25° C. In an embodiment of the present invention, the water solubility of Reb. D at a water temperature of 25° C. is 75 mg/100 g-$H_2O$ or higher. In another embodiment of the present invention, the water solubility of Reb. D at a water temperature of 25° C. is 80 mg/100 g-H$_2$O or higher, 85 mg/100 g-H$_2$O or higher, 90 mg/100 g-H$_2$O or higher, 95 mg/100 g-H$_2$O or higher, 100 mg/100 g-H$_2$O or higher, 110 mg/100 g-H$_2$O or higher, 120 mg/100 g-H$_2$O or higher, 130 mg/100 g-H$_2$O or higher, 140 mg/100 g-H$_2$O or higher, 150 mg/100 g-H$_2$O or higher, 160 mg/100 g-H$_2$O or higher, 170 mg/100 g-H$_2$O or higher, 180 mg/100 g-H$_2$O or higher, 190 mg/100 g-H$_2$O or higher, 200 mg/100 g-H$_2$O or higher, 250 mg/100 g-H$_2$O or higher, 300 mg/100 g-H$_2$O or higher, 350 mg/100 g-H$_2$O or higher, 400 mg/100 g-H$_2$O or higher, 450 mg/100 g-H$_2$O or higher, 500 mg/100 g-H$_2$O or higher, 550 mg/100 g-H$_2$O or higher, 600 mg/100 g-H$_2$O or higher, 650 mg/100 g-H$_2$O or higher, or 700 mg/100 g-H$_2$O or higher. The upper limit of the solubility at a water temperature of 25° C. is preferably 800 mg/100 g-H$_2$O or lower, 750 mg/100 g-H$_2$O or lower, 700 mg/100 g-H$_2$O or lower, 650 mg/100 g-H$_2$O or lower, or 600 mg/100 g-H$_2$O or lower. In another embodiment of the present invention, the water solubility of Reb. D at a water temperature of 25° C. may be 75 mg/100 g-H$_2$O to 800 mg/100 g-H$_2$O, 100 mg/100 g-H$_2$O to 800 mg/100 g-H$_2$O, 150 mg/100 g-H$_2$O to 800 mg/100 g-H$_2$O, 200 mg/100 g-H$_2$O to 800 mg/100 g-H$_2$O, 250 mg/100 g-H$_2$O to 800 mg/100 g-H$_2$O, 300 mg/100 g-H$_2$O to 800 mg/100 g-H$_2$O, 350 mg/100 g-H$_2$O to 800 mg/100 g-H$_2$O, 400 mg/100 g-H$_2$O to 800 mg/100 g-H$_2$O, 450 mg/100 g-H$_2$O to 800 mg/100 g-H$_2$O, 500 mg/100 g-H$_2$O to 800 mg/100 g-H$_2$O, 550 mg/100 g-H$_2$O to 800 mg/100 g-H$_2$O, 600 mg/100 g-H$_2$O to 800 mg/100 g-H$_2$O, 650 mg/100 g-H$_2$O to 800 mg/100 g-H$_2$O, 700 mg/100 g-H$_2$O to 800 mg/100 g-H$_2$O, 75 mg/100 g-H$_2$O to 750 mg/100 g-H$_2$O, 100 mg/100 g-H$_2$O to 750 mg/100 g-H$_2$O, 150 mg/100 g-H$_2$O to 750 mg/100 g-H$_2$O, 200 mg/100 g-H$_2$O to 750 mg/100 g-H$_2$O, 250 mg/100 g-H$_2$O to 750 mg/100 g-H$_2$O, 300 mg/100 g-H$_2$O to 750 mg/100 g-H$_2$O, 350 mg/100 g-H$_2$O to 750 mg/100 g-H$_2$O, 400 mg/100 g-H$_2$O to 750 mg/100 g-H$_2$O, 450 mg/100 g-H$_2$O to 750 mg/100 g-H$_2$O, 500 mg/100 g-H$_2$O to 750 mg/100 g-H$_2$O, 550 mg/100 g-H$_2$O to 750 mg/100 g-H$_2$O, 600 mg/100 g-H$_2$O to 750 mg/100 g-H$_2$O, 650 mg/100 g-H$_2$O to 750 mg/100 g-H$_2$O, 700 mg/100 g-H$_2$O to 750 mg/100 g-H$_2$O, 75 mg/100 g-H$_2$O to 700 mg/100 g-H$_2$O, 100 mg/100 g-H$_2$O to 700 mg/100 g-H$_2$O, 150 mg/100 g-H$_2$O to 700 mg/100 g-H$_2$O, 200 mg/100 g-H$_2$O to 700 mg/100 g-H$_2$O, 250 mg/100 g-H$_2$O to 700 mg/100 g-H$_2$O, 300 mg/100 g-H$_2$O to 700 mg/100 g-H$_2$O, 350 mg/100 g-H$_2$O to 700 mg/100 g-H$_2$O, 400 mg/100 g-H$_2$O to 700 mg/100 g-H$_2$O, 450 mg/100 g-H$_2$O to 700 mg/100 g-H$_2$O, 500 mg/100 g-H$_2$O to 700 mg/100 g-H$_2$O, 550 mg/100 g-H$_2$O to 700 mg/100 g-H$_2$O, 600 mg/100 g-H$_2$O to 700 mg/100 g-H$_2$O, 650 mg/100 g-H$_2$O to 700 mg/100 g-H$_2$O, 75 mg/100 g-H$_2$O to 650 mg/100 g-H$_2$O, 100 mg/100 g-H$_2$O to 650 mg/100 g-H$_2$O, 150 mg/100 g-H$_2$O to 650 mg/100 g-H$_2$O, 200 mg/100 g-H$_2$O to 650 mg/100 g-H$_2$O, 250 mg/100 g-H$_2$O to 650 mg/100 g-H$_2$O, 300 mg/100 g-H$_2$O to 650 mg/100 g-H$_2$O, 350 mg/100 g-H$_2$O to 650 mg/100 g-H$_2$O, 400 mg/100 g-H$_2$O to 650 mg/100 g-H$_2$O, 450 mg/100 g-H$_2$O to 650 mg/100 g-H$_2$O, 500 mg/100 g-H$_2$O to 650 mg/100 g-H$_2$O, 550 mg/100 g-H$_2$O to 650 mg/100 g-H$_2$O, 600 mg/100 g-H$_2$O to 650 mg/100 g-H$_2$O, 150 mg/100 g-H$_2$O to 600 mg/100 g-H$_2$O, 200 mg/100 g-H$_2$O to 600 mg/100 g-H$_2$O, 250 mg/100 g-H$_2$O to 600 mg/100 g-H$_2$O, 300 mg/100 g-H$_2$O to 600 mg/100 g-H$_2$O, 150 mg/100 g-H$_2$O to 500 mg/100 g-H$_2$O, 200 mg/100 g-H$_2$O to 500 mg/100 g-H$_2$O, 250 mg/100 g-H$_2$O to 500 mg/100 g-H$_2$O, or 300 mg/100 g-H$_2$O to 500 mg/100 g-H$_2$O.

As used herein, "the solubility of Reb. D" means the amount (mg) of Reb. D dissolved in 100 g of water. In this specification, the solubility of Reb. D is a solubility at a water temperature of 25° C. unless otherwise stated. The amount of Reb. D dissolved in water can be confirmed by adding the complex to water to be dissolved therein while stirring until the complex is no longer dissolved in water and then measuring the amount of Reb. D dissolved in water. The amount of Reb. D dissolved in water can be measured by using liquid chromatograph mass spectrometry (LC-MC). In this specification, the value of the solubility is equal to or larger than that of the dissolution amount described in the Examples.

In an embodiment of the present invention, Reb. D in the complex is amorphous. "Amorphous" refers to a state of having no crystal structure, for example, a state of showing no clear peak when analyzing by means of X-ray crystal diffraction (XRD). As used herein, "Reb. D is amorphous" means a state in which no peak specific to Reb. D can be confirmed or the half width of a peak specific to Reb. D is larger than 0.5°. The peak specific to Reb. D refers to at least one selected from 6.5±0.2 deg, 10.3±0.2 deg, 20.4±0.2 deg and 20.0±0.2 deg. Reb. D can be made amorphous by various methods, but it is preferably made amorphous by melting at least one compound selected from carbohydrates and water-soluble vitamins and salts thereof and dissolving Reb. D therein, followed by performing cooling by stirring or static cooling, as described later with respect to the method for producing the complex of the present invention. Further, in another embodiment of the present invention, the amorphous Reb. D contained in the complex of the present invention excludes those obtained by the spray dry method (or spray cooling method).

The complex of the present invention contains, in addition to Reb. D, at least one compound selected from carbohydrates and water-soluble vitamins and salts thereof. The at least one compound selected from carbohydrates and water-soluble vitamins and salts thereof to be used in the complex of the present invention is not particularly limited as long as it is a compound, which is melted by heating at ordinary pressure under air atmosphere, and which forms a complex together with Reb. D, and which can improve the solubility of Reb. D. The carbohydrates are selected from sugars (e.g., monosaccharides and disaccharides), polysaccharides (e.g., oligosaccharide, dextrin and starch) and sugar alcohols (e.g., erythritol and sorbitol), and steviol glycosides such as Reb. D are not included therein. The water-soluble vitamins are selected from vitamins which are easily dissolved in water. In an embodiment of the present invention, the at least one compound selected from the carbohydrates and the water-soluble vitamins and the salts thereof is selected from sugars or sugar alcohols.

In an embodiment of the present invention, the at least one compound selected from the carbohydrates and the water-soluble vitamins and the salts thereof includes at least one selected from sucrose, fructose, maltose, xylitol, erythritol, maltitol, palatinose, mannose, arabinose, mannitol, lactitol, glucose, allulose (another name: psicose), xylose, rhamnose and ribose. Further, in another embodiment of the present invention, the sugar alcohols include at least one selected from erythritol, sorbitol, xylitol, mannitol, maltitol, isomaltitol, lactitol, maltotriitol, isomaltotriitol and panitol. In yet another embodiment of the present invention, the water-soluble vitamins and the salts thereof include at least one selected from sodium pantothenate, pantothenic acid (vitamin B5), vitamin B1, vitamin B2, vitamin B3, vitamin B6, vitamin B7, vitamin B9 and vitamin B12, and salts thereof.

In yet another embodiment of the present invention, the sugars include at least one selected from glucose, rhamnose, xylose, ribose, allulose, arabinose, mannose, fructose, sucrose, maltose and lactose. Note that the sugars to be used in an embodiment of the present invention may be either a D-type isomer or an L-type isomer, but a D-type isomer is preferred.

In an embodiment of the present invention, the complex of the present invention consists essentially of: Reb. D; and at least one compound selected from carbohydrates and water-soluble vitamins and salts thereof. As used herein, "consists essentially of . . . " means that the complex of the present invention may contain another structural unit in addition to Reb. D and the at least one compound selected from the carbohydrates and the water-soluble vitamins and the salts thereof within a range in which the effects of the invention are not reduced. Examples of such cases include the case where the complex contains impurities that are inevitably contained in Reb. D, the carbohydrates, the water-soluble vitamins or the salts of the water-soluble vitamins, and the case where the complex contains a component other than Reb. D, the carbohydrates, the water-soluble vitamins and the salts of the water-soluble vitamins in an amount of 0 to 5% by weight, 0 to 4% by weight, 0 to 3% by weight, 0 to 2% by weight or 0 to 1% by weight relative to the total amount of the complex. Further, for example, when producing the complex of the present invention by melting at least one compound selected from carbohydrates and water-soluble vitamins and salts thereof and dissolving Reb. D therein, the presence of impurities that are inevitably mixed and Reb. B that is generated by decomposition of Reb. D is allowed, as described later with respect to the method for producing the complex of the present invention.

In an embodiment of the present invention, the content of Reb. D in the complex is an amount equal to or less than the saturation solubility relative to the at least one compound selected from the carbohydrates and the water-soluble vitamins and the salts thereof. The saturation solubility means an amount (mg) with which Reb. D is no longer dissolved in a melt of 1 g of the at least one compound selected from the carbohydrates and the water-soluble vitamins and the salts thereof. The saturation solubility varies depending on the type of the compound and the temperature of the melt, but can be easily and accurately confirmed by actually forming a melt and dissolving Reb. D therein. For example, when forming a melt by using erythritol, 112 mg of Reb. D is dissolved in 1 g of erythritol at 190° C. (i.e., 112 mg/g).

In an embodiment of the present invention, the content of Reb. D in the complex may be 10 to 300 mg, 20 to 290 mg, 30 to 280 mg, 40 to 270 mg, 50 to 260 mg, 60 to 250 mg, 70 to 240 mg, 80 to 230 mg, 90 to 200 mg, 10 to 200 mg, 20 to 200 mg, 30 to 200 mg, 40 to 200 mg, 50 to 200 mg, 60 to 200 mg, 70 to 200 mg, 80 to 200 mg, 10 to 150 mg, 20 to 150 mg, 30 to 150 mg, 40 to 150 mg, 50 to 150 mg, 60 to 150 mg, 70 to 150 mg, 80 to 150 mg, 90 to 150 mg, 10 to 100 mg, 20 to 100 mg, 30 to 100 mg, 40 to 100 mg, 50 to 100 mg, 10 to 80 mg, 20 to 80 mg, 30 to 80 mg, 40 to 80 mg or 50 to 80 mg relative to 1 g of the at least one compound selected from the carbohydrates and the water-soluble vitamins and the salts thereof.

In an embodiment of the present invention, the complex contains Reb. D and erythritol, and the content of Reb. D may be 10 to 300 mg, 20 to 290 mg, 30 to 280 mg, 40 to 270 mg, 50 to 260 mg, 60 to 250 mg, 70 to 240 mg, 80 to 230 mg, 90 to 200 mg, 10 to 200 mg, 20 to 200 mg, 30 to 200 mg, 40 to 200 mg, 50 to 200 mg, 60 to 200 mg, 70 to 200 mg, 80 to 200 mg, 10 to 150 mg, 20 to 150 mg, 30 to 150 mg, 40 to 150 mg, 50 to 150 mg, 60 to 150 mg, 70 to 150 mg, 80 to 150 mg, 90 to 150 mg, 10 to 100 mg, 20 to 100 mg, 30 to 100 mg, 40 to 100 mg, 50 to 100 mg, 10 to 80 mg, 20 to 80 mg, 30 to 80 mg, 40 to 80 mg or 50 to 80 mg, and is preferably 10 to 100 mg, and more preferably 20 to 80 mg relative to 1 g of erythritol.

In an embodiment of the present invention, the complex contains Reb. D, erythritol and fructose, and the content of Reb. D may be 10 to 300 mg, 20 to 290 mg, 30 to 280 mg, 40 to 270 mg, 50 to 260 mg, 60 to 250 mg, 70 to 240 mg, 80 to 230 mg, 90 to 200 mg, 10 to 200 mg, 20 to 200 mg, 30 to 200 mg, 40 to 200 mg, 50 to 200 mg, 60 to 200 mg, 70 to 200 mg, 80 to 200 mg, 10 to 150 mg, 20 to 150 mg, 30 to 150 mg, 40 to 150 mg, 50 to 150 mg, 60 to 150 mg, 70 to 150 mg, 80 to 150 mg, 90 to 150 mg, 10 to 100 mg, 20 to 100 mg, 30 to 100 mg, 40 to 100 mg, 50 to 100 mg, 10 to 80 mg, 20 to 80 mg, 30 to 80 mg, 40 to 80 mg or 50 to 80 mg, and is preferably 10 to 100 mg, and more preferably 20 to 80 mg relative to 1 g of the total of erythritol and fructose.

In an embodiment of the present invention, the complex contains Reb. D, erythritol and fructose, and the weight ratio between the content of erythritol and the content of fructose may be 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, 1.5:1 to 1:1.5, 10:1 to 1:1, 9:1 to 1:1, 8:1 to 1:1, 7:1 to 1:1, 6:1 to 1:1, 5:1 to 1:1, 4:1 to 1:1, 3:1 to 1:1, 2:1 to 1:1, 1.5:1 to 1:1, 9:1 to 2:1, 8:1 to 3:1 or 7:1 to 4:1, and is preferably 9:1 to 2:1, and more preferably 8:1 to 3:1.

In an embodiment of the present invention, the at least one compound selected from the carbohydrates and the water-soluble vitamins and the salts thereof is erythritol, and the complex of the present invention has a peak at at least one selected from $2\theta=14.8\pm0.2$ deg, $20.2\pm0.2$ deg, $24.5\pm0.2$ deg and $27.9\pm0.2$ deg in X-ray diffraction (CuKα: λ=1.5405 Å). In a preferred embodiment, the complex of the present invention has a peak at at least two, at least three or all the positions selected from those described above. In another embodiment of the present invention, the complex of the present invention further has a peak at at least one selected from $19.5\pm0.2$ deg, $28.3\pm0.2$ deg, $29.5\pm0.2$ deg, $31.1\pm0.2$ deg and $32.7\pm0.2$ deg.

In an embodiment of the present invention, the complex of the present invention includes a eutectic crystal of Reb. D and at least one compound selected from carbohydrates and water-soluble vitamins and salts thereof. A eutectic crystal is a substance obtained when a mixed liquid of two or more components solidifies at a constant melting point like a pure substance to form a mixed solid having the same composition. In the present invention, it is inferred that a eutectic crystal is formed by heating and melting at least one compound selected from carbohydrates and water-soluble vitamins and salts thereof and then dissolving Reb. D in the obtained melt, followed by cooling and solidifying it using an appropriate method. A eutectic crystal is formed with two or more components at a predetermined ratio (eutectic composition). In an embodiment of the present invention, it is not required that the complex of the present invention is entirely eutectic, and a part of the complex may be eutectic. For example, in the process of cooling a melt in which Reb. D is dissolved, a component that is precipitated before reaching a eutectic point may be contained. While not wishing to be bound by theory, it is inferred that the solubility is improved when the state of Reb. D is changed by formation of a eutectic crystal.

2. Sweetener Composition Containing the Complex of the Present Invention

According to an aspect of the present invention, a sweetener composition containing the complex of the present invention (hereinafter also referred to as "the sweetener composition of the present invention") is provided. The sweetener composition of the present invention is not particularly limited as long as it contains the complex of the present invention.

The amount of the complex of the present invention contained in the sweetener composition of the present invention is not particularly limited, but for example, it is 50 to 100%, preferably 80 to 100%, and more preferably 95 to 100%. The amount of the complex of the present invention contained in the sweetener composition of the present invention is the ratio (wt %) of the weight of the complex of the present invention to the total weight of the sweetener composition.

The sweetener composition of the present invention may further contain another steviol glycoside in addition to the complex of the present invention. For example, the sweetener composition of the present invention may further contain, in addition to the complex of the present invention, at least one steviol glycoside selected from the group consisting of rebaudioside A (Reb. A), rebaudioside B (Reb. B), rebaudioside C (Reb. C), rebaudioside E (Reb. E), rebaudioside F (Reb. F), rebaudioside G (Reb. G), rebaudioside I (Reb. I), rebaudioside J (Reb. J), rebaudioside K (Reb. K), rebaudioside M (Reb. M), rebaudioside N (Reb. N), rebaudioside O (Reb. O), rebaudioside Q (Reb. Q), rebaudioside R (Reb. R), rebaudioside V (Reb. V), rebaudioside W (Reb. W), rebaudioside KA (Reb. KA), dulcoside A, rubusoside, steviol, steviolmonoside, steviolbioside and stevioside.

The sweetener composition of the present invention may further contain another sweetener. Examples of the another sweetener include: natural sweeteners such as cane sugar (sucrose), high fructose corn syrup, Mogroside V, xylitol, corn syrup, fructose, sugar, glucose, maltose, high fructose syrup, sugar alcohols (xylitol, erythritol, etc.), oligosaccharide, honey, sugarcane juice (brown sugar syrup), starch syrup, luo han guo powder, luo han guo extract, licorice powder, licorice extract, *Thaumatococcus danielli* seed powder and *Thaumatococcus danielli* seed extract; and artificial sweeteners such as acesulfame potassium, sucralose, neotame, aspartame and saccharin. Among them, from the viewpoint of imparting cleanness, ease of drinking, natural taste and moderate rich taste, natural sweeteners are preferably used, and fructose, glucose, maltose, sucrose and sugar are particularly preferably used. These sweetness components may be used solely, or two or more of them may be used in combination.

In an embodiment of the present invention, the sweetener composition of the present invention further contains at least one selected from the group consisting of Reb. A, Reb. B, Reb. C, Reb. E, Reb. F, Reb. G, Reb. I, Reb. J, Reb. K, Reb. M, Reb. N, Reb. O, Reb. Q, Reb. R, Reb. V, Reb. W, Reb. KA, dulcoside A, rubusoside, steviol, steviolmonoside, steviolbioside, stevioside, sucrose, high fructose corn syrup, erythritol, Mogroside V, corn syrup, aspartame, sucralose, acesulfame potassium, saccharin and xylitol.

When the another steviol glycoside or another high intensity sweetener (e.g., Mogroside V, xylitol and artificial sweeteners) is contained, the composition ratio (weight ratio) between Reb. D and the another steviol glycoside or another high intensity sweetener in the complex of the present invention may be 1:99 to 99:1, 5:99 to 95:5, 10:90 to 90:10, 15:85 to 85:15, 20:80 to 80:20, 25:75 to 75:25, 30:70 to 70:30, 35:65 to 65:35, 40:60 to 60:40, 45:65 to 65:45, or 50:50. When a low intensity sweetener (e.g., sucrose, high fructose corn syrup, etc.) is contained in the sweetener composition of the present invention, the composition ratio (weight ratio) between Reb. D and the low intensity sweetener in the complex of the present invention may be 1:1000 to 1:100, 1:800 to 1:100, 1:700 to 1:100, 1:600 to 1:100, 1:500 to 1:100, 1:400 to 1:100, 1:300 to 1:100, or 1:200 to 1:100.

Examples of the sweetener composition of the present invention include, but are not limited to, a tabletop functional sweetener composition, a concentrate for beverages, a sweetness enhancing agent and a flavor controlling agent.

When the sweetener composition of the present invention is used as a concentrate for beverages, it may be used for beverages by dilution at any dilution rate. In this case, it can be used by being diluted 2-fold, 3-fold, 4-fold, 5-fold, 6-fold, 7-fold, 8-fold, 9-fold or 10-fold with water or carbonated water. Further, the concentrate for beverages is preferred in terms of storageability and transportability because it is concentrated. When using the sweetener composition of the present invention as the concentrate for beverages, it may be either solid or liquid.

When the sweetener composition according to an embodiment of the present invention is used as the concentrate for beverages, the Brix of the concentrate may be more than 15 but 50 or less, 20 to 50, 25 to 50, 30 to 50, 35 to 50, 40 to 50, 20 to 40, 25 to 40, 30 to 40, 20 to 35, or 20 to 30. The Brix of the concentrate can be calculated from the sweetness of each sweetener such as a steviol glycoside relative to cane sugar (sucrose) and the content of each sweetener as in the case of the Brix of beverages which will be described later.

3. Food or Beverage Containing the Complex or Sweetener Composition of the Present Invention According to an aspect of the present invention, a food or beverage containing the complex or sweetener composition of the present invention (hereinafter also referred to as "the food or beverage of the present invention") is provided. The food or beverage of the present invention is not particularly limited as long as it contains the complex or sweetener composition of the present invention. In this regard, the food or beverage means beverages and foods.

The amount of Reb. D contained in the food or beverage of the present invention varies depending on the specific type of the food or beverage, but it is preferably within a range roughly from 10 mass ppm to 600 mass ppm, and for example, it may be 20 mass ppm to 550 mass ppm, 25 mass ppm to 550 mass ppm, 30 mass ppm to 550 mass ppm, 35 mass ppm to 550 mass ppm, 40 mass ppm to 550 mass ppm, 45 mass ppm to 550 mass ppm, 50 mass ppm to 550 mass ppm, 55 mass ppm to 550 mass ppm, 20 mass ppm to 540 mass ppm, 25 mass ppm to 540 mass ppm, 30 mass ppm to 540 mass ppm, 35 mass ppm to 540 mass ppm, 40 mass ppm to 540 mass ppm, 45 mass ppm to 540 mass ppm, 50 mass ppm to 540 mass ppm, 55 mass ppm to 540 mass ppm, 20 mass ppm to 530 mass ppm, 25 mass ppm to 530 mass ppm, 30 mass ppm to 530 mass ppm, 35 mass ppm to 530 mass ppm, 40 mass ppm to 530 mass ppm, 45 mass ppm to 530 mass ppm, 50 mass ppm to 530 mass ppm, 55 mass ppm to 530 mass ppm, 20 mass ppm to 520 mass ppm, 25 mass ppm to 520 mass ppm, 30 mass ppm to 520 mass ppm, 35 mass ppm to 520 mass ppm, 40 mass ppm to 520 mass ppm, 45 mass ppm to 520 mass ppm, 50 mass ppm to 520 mass ppm, 55 mass ppm to 520 mass ppm, 20 mass ppm to 510 mass ppm, 25 mass ppm to 510 mass ppm, 30 mass ppm to 510 mass ppm, 35 mass ppm to 510 mass ppm, 40 mass ppm to 510 mass ppm, 45 mass ppm to 510 mass ppm, 50 mass ppm to 510 mass ppm, 55 mass ppm to 510 mass ppm, 20 mass ppm to 505 mass ppm, 25 mass ppm to 505 mass ppm, 30 mass ppm to 505 mass ppm, 35 mass ppm to 505 mass ppm, 40 mass ppm to 505 mass ppm, 45 mass ppm to 505 mass ppm, 50 mass ppm to 505 mass ppm, 55 mass ppm to 505 mass ppm, 20 mass ppm to 500 mass ppm, 25 mass ppm to 500 mass ppm, 30 mass ppm to 500 mass ppm, 35 mass ppm to 500 mass ppm, 40 mass ppm to 500 mass ppm, 45 mass ppm to 500 mass ppm, 50 mass ppm to 500 mass ppm, 55 mass ppm to 500 mass ppm, 20 mass ppm to 495 mass ppm, 25 mass ppm to 495 mass ppm, 30 mass ppm to 495 mass ppm, 35 mass ppm to 495 mass ppm, 40 mass ppm to 495 mass ppm, 45 mass ppm to 495 mass ppm, 50 mass ppm to 495 mass ppm, 55 mass ppm to 495 mass ppm, 20 mass ppm to 490 mass ppm, 25 mass ppm to 490 mass ppm, 30 mass ppm to 490 mass ppm, 35 mass ppm to 490 mass ppm, 40 mass ppm to 490 mass ppm, 45 mass ppm to 490 mass ppm, 50 mass ppm to 490 mass ppm, 55 mass ppm to 490 mass ppm, 100 mass ppm to 400 mass ppm, 150 mass ppm to 400 mass ppm, 200 mass ppm to 400 mass ppm, 250 mass ppm to 400 mass ppm, 300 mass ppm to 400 mass ppm, 100 mass ppm to 150 mass ppm, 100 mass ppm to 200 mass ppm, 100 mass ppm to 250 mass ppm, or 100 mass ppm to 300 mass ppm. When the content is adjusted within the above-described ranges, it is advantageous on the point that moderate sweetness can be imparted to the food or beverage.

The food or beverage of the present invention may further contain another steviol glycoside in addition to the complex or sweetener composition of the present invention. For example, the food or beverage of the present invention may further contain, in addition to the complex or sweetener composition of the present invention, at least one steviol glycoside selected from the group consisting of rebaudioside A (Reb. A), rebaudioside B (Reb. B), rebaudioside C (Reb. C), rebaudioside E (Reb. E), rebaudioside F (Reb. F), rebaudioside G (Reb. G), rebaudioside I (Reb. I), rebaudioside J (Reb. J), rebaudioside K (Reb. K), rebaudioside M (Reb. M), rebaudioside N (Reb. N), rebaudioside O (Reb. O), rebaudioside Q (Reb. Q), rebaudioside R (Reb. R), rebaudioside V (Reb. V), rebaudioside W (Reb. W), rebaudioside KA (Reb. KA), dulcoside A, rubusoside, steviol, steviolmonoside, steviolbioside and stevioside.

The food or beverage of the present invention may further contain another sweetener. Examples of the another sweetener include: natural sweeteners such as cane sugar (sucrose), high fructose corn syrup, Mogroside V, xylitol, corn syrup, fructose, sugar, glucose, maltose, high fructose syrup, sugar alcohols (xylitol, erythritol, etc.), oligosaccharide, honey, sugarcane juice (brown sugar syrup), starch syrup, luo han guo powder, luo han guo extract, licorice powder, licorice extract, *Thaumatococcus danielli* seed powder and *Thaumatococcus danielli* seed extract; and artificial sweeteners such as acesulfame potassium, sucralose, neotame, aspartame and saccharin. Among them, from the viewpoint of imparting cleanness, ease of drinking, natural taste and moderate rich taste, natural sweeteners are preferably used, and fructose, glucose, maltose, sucrose and sugar are particularly preferably used. These sweetness components may be used solely, or two or more of them may be used in combination. These sweeteners may be contained in a beverage in an amount (Brix conversion) of 5.0 or less, 4.5 or less, 4.0 or less, 3.5 or less, 3.0 or less, 2.5 or less, 2.0 or less, 1.5 or less, 1.0 or less, or 0.5 or less, and the lower limit may be 0.1 or more.

In an embodiment of the present invention, the food or beverage of the present invention further contains at least one selected from the group consisting of Reb. A, Reb. B, Reb. C, Reb. E, Reb. F, Reb. G, Reb. I, Reb. J, Reb. K, Reb. M, Reb. N, Reb. O, Reb. Q, Reb. R, Reb. V, Reb. W, Reb. KA, dulcoside A, rubusoside, steviol, steviolmonoside, steviolbioside, stevioside, sucrose, high fructose corn syrup, erythritol, Mogroside V, corn syrup, aspartame, sucralose, acesulfame potassium, saccharin and xylitol.

The food of the present invention is not particularly limited, and examples thereof include confectioneries, breads, flours, noodles, cooked rices, processed agricultural/forest products, processed livestock products, processed marine products, milk/dairy products, oils and fats/oil-and-fat processed products, seasonings and other food materials.

The beverage of the present invention is not particularly limited, and examples thereof include carbonated beverages, non-carbonated beverages, alcohol beverages, non-alcoholic beverages, coffee beverages, tea beverages, cocoa-based beverages, nutritional beverages, functional beverages, fruit/vegetable-based beverages and lactic beverages.

In an embodiment of the present invention, the beverage may be a non-alcoholic beer. The non-alcoholic beer means a carbonated beverage having a beer-like flavor. It is a non-fermented non-alcoholic type and substantially does not contain alcohol. In this regard, beverages containing a very small amount of alcohol that cannot be detected are not excluded from the non-alcoholic beer.

In the case where the beverage according to an embodiment of the present invention is a tea beverage, it is preferably a black tea beverage or a sugar-free tea beverage. Examples of the sugar-free tea beverage include green tea beverages, oolong tea beverages, barley tea beverages, brown rice tea beverages, adlay tea beverages and sugar-free black tea beverages. The coffee beverage may be either container-packed coffee or liquid coffee.

In the case where the beverage according to an embodiment of the present invention is a carbonated beverage, it is preferably a cola-flavored beverage, a transparent carbonated beverage, ginger ale, a fruit juice-based carbonated beverage, a milk-containing carbonated beverage or a sugar-free carbonated beverage. The nutritional beverages and functional beverages include sports beverages, energy beverages, health support beverages, and jelly beverages contained in pouches.

In the case where the beverage according to an embodiment of the present invention is a fruit/vegetable-based beverage, examples thereof include 100% fruit beverages, fruit-containing beverages, low fruit juice-content refreshing beverages, fruit granule-containing fruit beverages or fruit pulp-containing beverages. The lactic beverages include milk, beverage yogurt, lactic acid bacteria beverages or milk-containing refreshing beverages, and soymilk beverages include soymilk or soybean beverages.

The alcohol beverage refers to a beverage containing an alcoholic raw material. It may be a cocktail (e.g., chu-hi (shochu-based beverage)) using distilled liquor (e.g., shochu (Japanese distilled spirit)). Examples of the alcoholic raw material include a brewage, a distilled liquor and a mixed liquor. Examples of the brewage include wine and beer. Examples of the distilled liquor include spirits (e.g., gin, vodka, rum, tequila, new spirits, alcohols for raw materials, etc.), liqueurs, whiskeys (e.g., whiskey, brandy, etc.) and shochu (Japanese distilled spirit). In this regard, the alcohol beverage may be one containing alcohol at a detectable level and contains, for example, 1% by volume or more, 2% by volume or more, 3% by volume or more, 4% by volume or more, or 5% by volume or more of alcohol.

The Brix of the beverage of the present invention is not particularly limited, but it is preferably 3 to 15, more preferably 5 to 13, and even more preferably 7 to 11. In this regard, the Brix can be calculated from the sweetness of each sweetener such as a steviol glycoside relative to cane sugar (sucrose) and the content of each sweetener. The sweetnesses of Reb. B, Reb. A, Reb. D and Reb. M are respectively 300 to 350 times, 200 to 450 times, 200 to 300 times, and 200 to 300 times that of sucrose. Accordingly, the amounts of a steviol glycoside corresponding to Brix 1 in Reb. B, Reb. A and Reb. D (the same for Reb. M) are respectively 30.7 ppm, 30.7 ppm, and 40.0 ppm according to calculation in which central values of the respective sweetnesses are used. Also, with respect to other steviol glycosides and sweeteners other than steviol glycosides, Brix can be calculated in the same way. For example, the sweetnesses of acesulfame potassium, sucralose and aspartame are respectively about 200 times, about 600 times, and about 180 times that of sucrose. Note that the relative ratio of the sweetness of various sweeteners to the sweetness of sucrose as 1 can be determined by using, for example, a publicly-known sugar sweetness-conversion table (e.g., "Inryo Yogo Jiten ("Dictionary of Beverage Terminology" in Japanese)", p. 11, published by Beverage Japan, Inc.). However, with respect to sweeteners whose values of the sweetness are described using numerical ranges and sweeteners whose values vary depending on literatures, the relative ratio of the sweetness to the sweetness of sucrose as 1 is determined by a sensory test. Examples of the sensory test include a method in which samples are prepared by adding sugar to each pure water in a manner such that the samples respectively have Brix of 3.0 to 5.0 in increments of 0.5 points; and among them, a sugar-added sample having a sweetness intensity equivalent to that of an aqueous solution of the sweetener having a predetermined concentration is selected.

In another embodiment of the present invention, the Brix of the beverage may be 10 or less, 9 or less, 8 or less, 7 or less, 6 or less, or 5 or less, and for example, it may be 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, or 6 to 7. In yet another embodiment of the present invention, the Brix of the beverage may be 10 to 15, 11 to 15, 12 to 15, 13 to 15, 14 to 15, 10 to 14, 10 to 13, 10 to 12, or 10 to 11, and such a beverage having a high Brix may be used as a concentrated stock solution of a beverage for dilution.

The energy (gross energy value) of the beverage of the present invention is not particularly limited, and it may be 0 to 50 Kcal/100 ml, 0 to 45 Kcal/100 ml, 0 to 40 Kcal/100 ml, 0 to 35 Kcal/100 ml, 0 to 30 Kcal/100 ml, 0 to 24 Kcal/100 ml, 0 to 22 Kcal/100 ml, 0 to 20 Kcal/100 ml, 0 to 15 Kcal/100 ml, 0 to 10 Kcal/100 ml, 0 to 5 Kcal/100 ml, 0.1 to 50 Kcal/100 ml, 0.1 to 45 Kcal/100 ml, 0.1 to 40 Kcal/100 ml, 0.1 to 35 Kcal/100 ml, 0.1 to 30 Kcal/100 ml, 0.1 to 24 Kcal/100 ml, 0.1 to 22 Kcal/100 ml, 0.1 to 20 Kcal/100 ml, 0.1 to 15 Kcal/100 ml, 0.1 to 10 Kcal/100 ml, 0.1 to 5 Kcal/100 ml, 1 to 50 Kcal/100 ml, 1 to 45 Kcal/100 ml, 1 to 40 Kcal/100 ml, 1 to 35 Kcal/100 ml, 1 to 30 Kcal/100 ml, 1 to 24 Kcal/100 ml, 1 to 22 Kcal/100 ml, 1 to 20 Kcal/100 ml, 1 to 15 Kcal/100 ml, 1 to 10 Kcal/100 ml, 1 to 5 Kcal/100 ml, 5 to 50 Kcal/100 ml, 5 to 45 Kcal/100 ml, 5 to 40 Kcal/100 ml, 5 to 35 Kcal/100 ml, 5 to 30 Kcal/100 ml, 5 to 24 Kcal/100 ml, 5 to 20 Kcal/100 ml, 5 to 15 Kcal/100 ml, 5 to 10 Kcal/100 ml, 10 to 50 Kcal/100 ml, 10 to 45 Kcal/100 ml, 10 to 40 Kcal/100 ml, 10 to 35 Kcal/100 ml, 10 to 30 Kcal/100 ml, 10 to 24 Kcal/100 ml, 10 to 20 Kcal/100 ml, 10 to 15 Kcal/100 ml, 15 to 50 Kcal/100 ml, 15 to 45 Kcal/100 ml, 15 to 40 Kcal/100 ml, 15 to 35 Kcal/100 ml, 15 to 30 Kcal/100 ml, 15 to 24 Kcal/100 ml, 15 to 20 Kcal/100 ml, 20 to 50 Kcal/100 ml, 20 to 45 Kcal/100 ml, 20 to 40 Kcal/100 ml, 20 to 35 Kcal/100 ml, 20 to 30 Kcal/100 ml, 20 to 24 Kcal/100 ml, 24 to 50 Kcal/100 ml, 24 to 45 Kcal/100 ml, 24 to 40 Kcal/100 ml, 24 to 35 Kcal/100 ml, or 24 to 30 Kcal/100 ml.

The beverage of the present invention may be prepared as a beverage which is heat-sterilized and packed in a container. The container is not particularly limited, and examples thereof include a plastic bottle, an aluminum can, a steel can, a paper pack, a chilled cup and a bottle. When heat sterilization is performed, the type thereof is not particularly limited, and an ordinary technique such as UHT sterilization and retort sterilization can be used. The temperature for the heat sterilization process is not particularly limited, but for example, it is 65 to 130° C., and preferably 85 to 120° C., and the time is 10 to 40 minutes. However, if a sterilization value equivalent to that obtained under the above-described conditions is obtained, sterilization may be performed at a suitable temperature for several seconds, for example, 5 to 30 seconds.

4. Method for Producing the Complex of the Present Invention

The complex of the present invention can be produced by a production method, which includes: heating at least one compound selected from carbohydrates and water-soluble vitamins and salts thereof to form a melt; dissolving Reb. D in the melt; and cooling the melt in which Reb. D is dissolved. While not wishing to be bound by theory, it is inferred that the solubility is improved because the state of Reb. D in the complex is changed by heating and melting at least one compound selected from carbohydrates and water-soluble vitamins and salts thereof and then dissolving Reb. D in the obtained melt, followed by cooling and solidifying it.

In the method for producing the complex of the present invention, formation of a melt can be suitably determined based on the melting point of the compound to be melted, but it is preferably carried out at a temperature lower than the decomposition point of Reb. D (about 250° C.). When a melt is formed at a temperature lower than the decomposition point of Reb. D, it is preferred on the point that the generation of Reb. B caused by decomposition of Reb. D can be suppressed thereby. In an embodiment of the present invention, a melt may be formed at a temperature 10° C. or more lower, 50° C. or more lower, or 100° C. or more lower than the decomposition point of Reb. D.

Formation of a melt can be carried out by heating at least one compound selected from carbohydrates and water-soluble vitamins and salts thereof using any publicly-known method. When heating, at least one compound selected from carbohydrates and water-soluble vitamins and salts thereof may be put into a heat-resistant container and heated using an oil bath or the like. Further, when the production is carried out on a greater scale, heating may be carried out using an extruder, a pressure-resistant tank, a tank in which oil is circulated through a jacket, or the like.

Heating may be carried out under air atmosphere, and the heating rate can be suitably selected. In an embodiment of the present invention, heating can be carried out at a heating rate of 1° C./min, 2° C./min, 3° C./min, 4° C./min, 5° C./min, 8° C./min, 10° C./min, 15° C./min or 20° C./min.

Reb. D to be used for producing the complex of the present invention is not particularly limited and may be a plant-derived product, a chemically synthesized product or a biosynthesized product. For example, Reb. D may be isolated from a plant body rich in Reb. D to be purified, or alternatively, Reb. D may be obtained by chemical synthesis or biosynthesis.

In the production method of the present invention, Reb. D is added to a melt obtained by heating at least one compound selected from carbohydrates and water-soluble vitamins and salts thereof, and Reb. D is dissolved in the melt. The dissolution of Reb. D may be carried out by (i) heating in a state where Reb. D and at least one compound selected from carbohydrates and water-soluble vitamins and salts thereof are mixed together in advance, or by (ii) heating at least one compound selected from carbohydrates and water-soluble vitamins and salts thereof to form a melt and then adding Reb. D thereto. The dissolution of Reb. D is regarded as sufficient when it cannot be visually confirmed that Reb. D remains in the melt. From the viewpoint of the improvement of the solubility, preferably, at least one compound selected from carbohydrates and water-soluble vitamins and salts thereof is heated to form a melt, and then Reb. D is added thereto. Further, by heating Reb. D in advance at about 100° C. for about 0.2 to 3 hours before it is dissolved in the melt, the time required for dissolving Reb. D in the melt can be further shortened. While not wishing to be bound by theory, it is inferred that the solubility is improved because the crystal form of Reb. D is changed by heating Reb. D at a predetermined temperature in advance. There is also a possibility that, even after cooling, crystallization occurs while Reb. D remains polymorphic in a solid phase, resulting in the improvement of the solubility.

In the production method of the present invention, the complex is obtained by cooling the melt in which Reb. D is dissolved. Cooling can be performed according to any publicly-known method. In a preferred embodiment of the present invention, cooling is preferably performed at a temperature equal to or lower than the nucleation temperature of at least one compound selected from carbohydrates and water-soluble vitamins and salts thereof (i.e., the compound constituting the melt). As used herein, the "nucleation temperature" means a temperature at which the crystal nucleus of at least one compound selected from carbohydrates and water-soluble vitamins and salts thereof that forms the melt is formed. For example, in the case where the melt is formed using erythritol, by performing cooling in a manner such that the solidification of erythritol starts at a temperature of 120° C. or lower, cooling can be performed at a temperature equal to or lower than the nucleation temperature. The solidification of erythritol may be performed at a temperature of 110° C. or lower, 100° C. or lower, 90° C. or lower, 80° C. or lower, 70° C. or lower, 60° C. or lower, 50° C. or lower, 40° C. or lower, 30° C. or lower, 20° C. or lower, 10° C. or lower, 0° C. or lower, −10° C. or lower, −20° C. or lower, −30° C. or lower, −40° C. or lower, −50° C. or lower, −60° C. or lower, −70° C. or lower, −80° C. or lower, −90° C. or lower, −100° C. or lower, −110° C. or lower, −120° C. or lower, −130° C. or lower, −140° C. or lower, −150° C. or lower, −160° C. or lower, −170° C. or lower, −180° C. or lower, −190° C. or lower, or −200° C. or lower.

The adjustment of the nucleation temperature is not particularly limited, and examples thereof include cooling the melt under an environment at a constant temperature and use of a seed crystal. As the seed crystal, the compound constituting the melt (e.g., erythritol) is preferably used. The particle diameter of the seed crystal is not particularly limited. When cooling the melt under an environment at a constant temperature, a water bath, an oil bath, a thermostatic bath, ice, dry ice, liquid nitrogen or the like may be used. Alternatively, when cooling the melt, a steel belt, a drum flaker, an extruder or the like may be used.

In another embodiment, cooling of the melt may be carried out under an environment in which a predetermined temperature is set. For example, cooling may be carried out under an environment at a temperature of −196° C. to 100° C., −50° C. to 95° C., 0° C. to 90° C., 10° C. to 85° C., 20° C. to 80° C., 30° C. to 80° C., or 40° C. to 80° C. In a preferred embodiment of the present invention, cooling of the melt is carried out under an environment at a temperature of 40° C. to 80° C.

In the production method of the present invention, cooling can be carried out at a cooling rate of 1.0° C./min, 2.0° C./min, 3.0° C./min, 4.0° C./min, 5.0° C./min, 6.0° C./min, 7.0° C./min, 8.0° C./min, 9.0° C./min, 10° C./min, 11° C./min, 12° C./min, 13° C./min, 14° C./min, 15° C./min or 20° C./min. Regarding the cooling rate, for example, the average cooling rate for 30 minutes from the start of cooling may be 0.5° C./min to 20° C./min, 0.5° C./min to 15° C./min, 0.5° C./min to 13° C./min, 0.5° C./min to 11° C./min, 0.5° C./min to 10° C./min, 0.5° C./min to 9.0° C./min, 0.5° C./min to 8.0° C./min, 0.5° C./min to 7.0° C./min, 0.5° C./min to 6.0° C./min, 0.5° C./min to 5.0° C./min, 0.5° C./min to 4.0° C./min, 0.5° C./min to 3.0° C./min, 0.5° C./min to 2.0° C./min, 0.5° C./min to 1.5° C./min, 1.0° C./min to 20° C./min, 1.0° C./min to 15° C./min, 1.0° C./min to 13° C./min, 1.0° C./min to 11° C./min, 1.0° C./min to 10° C./min, 1.0° C./min to 9.0° C./min, 1.0° C./min to 8.0° C./min, 1.0° C./min to 7.0° C./min, 1.0° C./min to 6.0° C./min, 1.0° C./min to 5.0° C./min, 1.0° C./min to 4.0° C./min, 1.0° C./min to 3.0° C./min, 1.0° C./min to 2.0° C./min, 1.0° C./min to 1.5° C./min, 1.5° C./min to 20° C./min, 1.5° C./min to 15° C./min, 1.5° C./min to 13° C./min, 1.5° C./min to 11° C./min, 1.5° C./min to 1.5° C./min, 1.5° C./min to 9.0° C./min, 1.5° C./min to 8.0° C./min, 1.5° C./min to 7.0° C./min, 1.5° C./min to 6.0° C./min, 1.5° C./min to 5.0° C./min, 1.5° C./min to 4.0° C./min, 1.5° C./min to 3.0° C./min, or 1.5° C./min to 2.0° C./min, and it is preferably 1.0° C./min to 5.0° C./min, and preferably 1.5° C./min to 3.5° C./min. Alternatively, the average cooling rate for 5 minutes from the start of cooling may be 0.5° C./min to 20° C./min, 0.5° C./min to 15° C./min, 0.5° C./min to 13° C./min, 0.5° C./min to 11° C./min, 0.5° C./min to 10° C./min, 0.5° C./min to 9.0° C./min, 0.5° C./min to 8.0° C./min, 0.5° C./min to 7.0° C./min, 0.5° C./min to 6.0° C./min, 0.5° C./min to 5.0° C./min, 0.5° C./min to 4.0° C./min, 0.5° C./min to 3.0° C./min, 0.5° C./min to 2.0° C./min, 0.5° C./min to 1.5° C./min, 1.0° C./min to 20° C./min, 1.0° C./min to 15° C./min, 1.0° C./min to 13° C./min, 1.0° C./min to 11° C./min, 1.0° C./min to 10° C./min, 1.0° C./min to 9.0° C./min, 1.0° C./min to 8.0° C./min, 1.0° C./min to 7.0° C./min, 1.0° C./min to 6.0° C./min, 1.0° C./min to 5.0° C./min, 1.0° C./min to 4.0° C./min, 1.0° C./min to 3.0° C./min, 1.0° C./min to 2.0° C./min, 1.0° C./min to 1.5° C./min, 1.5° C./min to 20° C./min, 1.5° C./min to 15° C./min, 1.5° C./min to 13° C./min, 1.5° C./min to 11° C./min, 1.5° C./min to 1.5° C./min, 1.5° C./min to 9.0° C./min, 1.5° C./min to 8.0° C./min, 1.5° C./min to 7.0° C./min, 1.5° C./min to 6.0° C./min, 1.5° C./min to 5.0° C./min, 1.5° C./min to 4.0° C./min, 1.5° C./min to 3.0° C./min, or 1.5° C./min to 2.0° C./min, and it is preferably 1.0° C./min to 14° C./min. Alternatively, the average cooling rate for 60 minutes from the start of cooling may be 0.5° C./min to 20° C./min, 0.5° C./min to 15° C./min, 0.5° C./min to 13° C./min, 0.5° C./min to 11° C./min, 0.5° C./min to 10° C./min, 0.5° C./min to 9.0°

C./min, 0.5° C./min to 8.0° C./min, 0.5° C./min to 7.0° C./min, 0.5° C./min to 6.0° C./min, 0.5° C./min to 5.0° C./min, 0.5° C./min to 4.0° C./min, 0.5° C./min to 3.0° C./min, 0.5° C./min to 2.0° C./min, 0.5° C./min to 1.5° C./min, 1.0° C./min to 20° C./min, 1.0° C./min to 15° C./min, 1.0° C./min to 13° C./min, 1.0° C./min to 11° C./min, 1.0° C./min to 10° C./min, 1.0° C./min to 9.0° C./min, 1.0° C./min to 8.0° C./min, 1.0° C./min to 7.0° C./min, 1.0° C./min to 6.0° C./min, 1.0° C./min to 5.0° C./min, 1.0° C./min to 4.0° C./min, 1.0° C./min to 3.0° C./min, 1.0° C./min to 2.0° C./min, 1.0° C./min to 1.5° C./min, 1.5° C./min to 20° C./min, 1.5° C./min to 15° C./min, 1.5° C./min to 13° C./min, 1.5° C./min to 11° C./min, 1.5° C./min to 1.5° C./min, 1.5° C./min to 9.0° C./min, 1.5° C./min to 8.0° C./min, 1.5° C./min to 7.0° C./min, 1.5° C./min to 6.0° C./min, 1.5° C./min to 5.0° C./min, 1.5° C./min to 4.0° C./min, 1.5° C./min to 3.0° C./min, or 1.5° C./min to 2.0° C./min, and it is preferably 1.0° C./min to 5.0° C./min. While not wishing to be bound by theory, it is inferred that the crystal structure of a complex obtained is changed by changing the cooling time.

In the production method of the present invention, cooling is carried out by cooling by stirring or static cooling. In general, amorphization of Reb. D is carried out by the spray drying method. However, in the present invention, the spray drying method is not used, and cooling by stirring or static cooling is employed to solidify the melt. When employing cooling by stirring or static cooling, it is preferred on the point that not only high solubility can be realized, but also high stability can be realized.

EXAMPLES

Hereinafter, the present invention will be described in detail by way of working examples, but the content of the present invention is not limited thereto. In the working examples, unless otherwise stated, the measurement of the dissolution amount of Reb. D was carried out at room temperature and in this regard, an aqueous solution was not heated or cooled.

[Example A] Evaluation of Melting/Dissolution

The meltability of a raw material to be combined with Reb. D (hereinafter also referred to as "the auxiliary raw material") and the solubility of Reb. D were evaluated, and the auxiliary raw material with which the complex of the present invention can be obtained was examined. As the auxiliary raw material, raw materials described in the table below were selected from food additives that can be added to beverages. The raw materials used for forming the complex are as follows: Reb. D formulation (purity: 95% (w/w), manufactured by Jining Renewal and Joint International); D-allulose (purity: 99%+), arabinose (purity: 98%+), fructose (purity: 99%+), glucose (purity: 99%+), maltose monohydrate (purity: 95%+), mannitol (purity: 99%+), mannose (purity: 98%+), rhamnose (purity: 98%+), ribose (purity: 98%+), sucrose (purity: 99%+), xylitol (purity: 98%+) and xylose (purity: 98%+), trehalose dihydrate (purity: 98%+), sodium pantothenate (purity: 98%+) (each manufactured by NACALAI TESQUE, INC.); and erythritol (purity: 98% (w/w), manufactured by Mitsubishi-Chemical Foods Corporation). Also in the subsequent working examples, the raw materials described above were used unless otherwise stated.

TABLE 1

| Classification | Name | Melting point (° C.) |
|---|---|---|
| Sweetener (carbohydrate) | Sucrose | 186 |
| | Fructose | 103 |
| | Maltose | 102 |
| | Xylitol | 96 |
| | Erythritol | 121 |
| | Maltitol | 169 |
| | Mannose | 140 |
| | Arabinose | 160 |
| | Trehalose dihydrate | 97 |
| | Mannitol | 169 |
| | Glucose | 156 |
| | D-allulose | 109 |
| | Xylose | 150 |
| | Rhamnose | 123 |
| | Ribose | 87 |
| Acidulant | Adipic acid | 154 |
| | Citric acid (anhydrous) | 150 |
| | D-Tartaric acid | 170 |
| | DL-malic acid | 123 |
| Antioxidant | Catechin | 175 |
| Enrichment | L-ascorbic acid | 192 |
| | Vitamin D3 | 88 |
| | Calcium stearate | 180 |
| | Sodium pantothenate | 124 |
| | Vitamin P | 150 |
| Seasoning | L-glutamine | 186 |
| Emulsifier | Lecithin | 30 |

The auxiliary raw material described in Table 1 was mixed with 100 mg of Reb. D formulation (purity: 95% (w/w)) in a heat-resistant vial, the temperature was elevated to the melting point of the auxiliary raw material or higher, and it was confirmed whether or not the auxiliary raw material was melted. After melting of the auxiliary raw material and dissolution of the Reb. D formulation were visually confirmed, the mixture was rapidly cooled in ice and stored at 10° C. The weight of the auxiliary raw material was adjusted based on the amount that enables dissolution of Reb. D. The weight of D-allulose (another name: D-psicose) was 2,000 mg, the weight of L-glutamine was 1,000 mg, the weight of vitamin D3 was 1,144 mg, and the weight of an auxiliary raw material other than those was 4,000 mg. The results are shown in Table 2. The case where it was recognized that the auxiliary raw material was melted and that Reb. D was dissolved (including the case where dissolution was visually recognized more when compared to the point of adding (complete dissolution is not required)) was evaluated as "O", and the case where it was not recognized that the auxiliary raw material was melted even at a temperature equal to or higher than the melting point of the auxiliary raw material, or the case where it was not recognized that Reb. D was dissolved though the auxiliary raw material was successfully melted (after the addition, change in outer appearance was not visually recognized) was evaluated as "X". Note that in the case of sucrose, coloring (caramel color) was recognized, and in the case of maltose, foaming was recognized. Further, in the case of rhamnose or xylose, the mixture became like candy-paste after cooling.

TABLE 2

| Classification | Name | Melting/ dissolution |
|---|---|---|
| Sweetener (carbohydrate) | Sucrose | O |
| | Fructose | O |
| | Maltose | O |
| | Xylitol | O |

TABLE 2-continued

| Classification | Name | Melting/dissolution |
|---|---|---|
| | Erythritol | ○ |
| | Maltitol | ○ |
| | Mannose | ○ |
| | Arabinose | ○ |
| | Trehalose | X |
| | Mannitol | ○ |
| | Glucose | ○ |
| | D-allulose | ○ |
| | Xylose | ○ |
| | Rhamnose | ○ |
| | Ribose | ○ |
| Acidulant | Adipic acid | ○ |
| | Citric acid (anhydrous) | ○ |
| | D-Tartaric acid | X |
| | DL-malic acid | ○ |
| Antioxidant | Catechin | X |
| Enrichment | L-ascorbic acid | X |
| | Vitamin D3 | ○ |
| | Calcium stearate | X |
| | Sodium pantothenate | ○ |
| | Vitamin P | X |
| Seasoning | L-glutamine | ○ |
| Emulsifier | Lecithin | X |

[Example B] Evaluation of Solubility

Regarding the samples of Example A, regarding which melting of the auxiliary raw material and dissolution of Reb. D were recognized, water solubility thereof was evaluated. Firstly, 13 ml of pure water was added to the complex obtained by dissolving the Reb. D formulation in the melted auxiliary raw material, and complete dissolution was carried out while stirring with a stirrer. Note that in the case of D-allulose, vitamin D3 or L-glutamine, 6.5 ml of pure water was added. After that, filtration was carried out with a 0.45 μm filter (manufactured by TOSC Japan Ltd.). Finally, the concentration of Reb. D contained in the filtrate was analyzed using a liquid chromatograph mass spectrometer (LCMS) ("LCMS 8050" manufactured by Shimadzu Corporation). The results are shown in FIG. 2.

Regarding many auxiliary raw materials tested this time, it was found that dissolution of Reb. D in the melted auxiliary raw material is effective in improving the solubility of Reb. D.

[Example C] Evaluation of Flavor

Evaluation of flavor was made with respect to the Reb. D/mannose complex, Reb. D/sucrose complex, Reb. D/xylitol complex, Reb. D/allulose complex, Reb. D/erythritol complex, Reb. D/rhamnose complex and Reb. D/xylose complex obtained in Example B.

Figure 3:
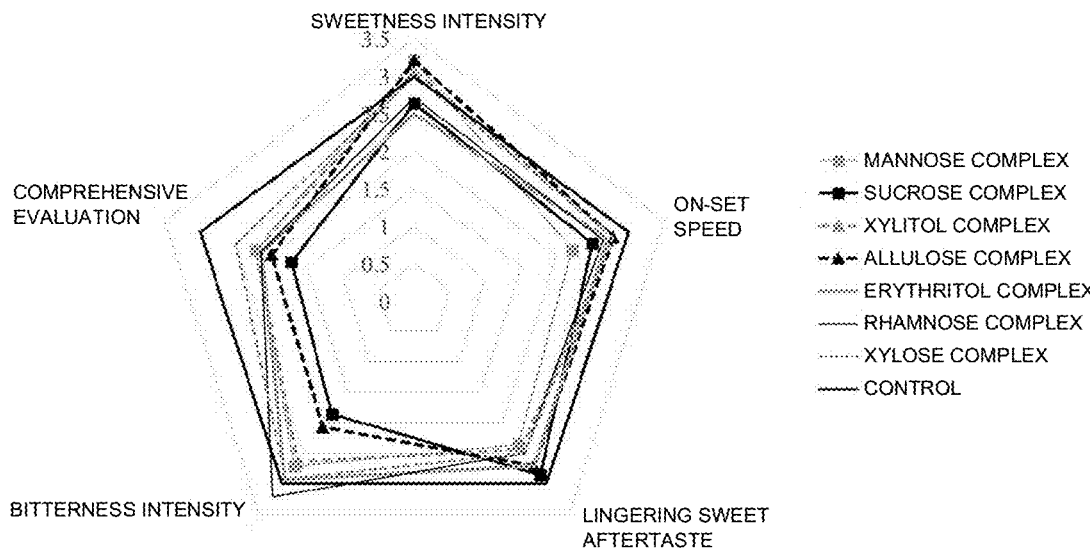
FIG. 3 shows the results of evaluation of flavor in Example C.

From the concentration of Reb. D contained in the filtrate obtained in Example B, the sweetness intensity of Reb. D was converted as 220 times the sweetness of sucrose, and dilution was carried out with pure water in a manner such that the sweetness in terms of sucrose became 5%. Evaluation of flavor was made by panelists trained about sensory attributes of sweeteners (7 members) (N=7). The results are shown in FIG. 3. The respective items of evaluation of flavor (sweetness intensity, on-set speed, lingering sweet aftertaste, bitterness intensity and comprehensive evaluation) were scored in increments of 0.5 points in a range of 0 to 6 points. 0 point means low sweetness intensity, low on-set speed, long lingering sweet aftertaste, high bitterness intensity and poor overall evaluation, and 6 points means high sweetness intensity, high on-set speed, short lingering sweet aftertaste, low bitterness intensity and satisfactory overall evaluation. As a reference, evaluation with respect to a solution in which the sweetness of sucrose alone in terms of sucrose is 5% (corresponding to Brix of 5) was used as a control (3 points).

[Example D] Reconfirmation of Improvement of Solubility of Reb. D by Melting

Regarding the Reb. D/erythritol complex (100 mg of Reb. D formulation, 4 g of erythritol, the same raw materials as those in Example A were used) that was highly evaluated in Example C, the solubility thereof was compared to those of Reb. D alone (Reb. D formulation only) and a composition obtained by simply mixing the Reb. D formulation and erythritol (hereinafter also referred to as "the Reb. D/erythritol composition"). Preparation of the Reb. D/erythritol composition by means of simple mixing and confirmation of the solubility were carried out by the below-described procedure.

(1) 100 mg of Reb. D is mixed with 4 g of erythritol.
(2) 13 ml of pure water is added thereto at room temperature, and stirring is performed at 500 rpm for 40 minutes.
(3) Sampling is carried out, filtration is carried out with a 0.45 μm filter, and then the concentration of Reb. D in a filtrate is measured by LCMS.

Figure 4:
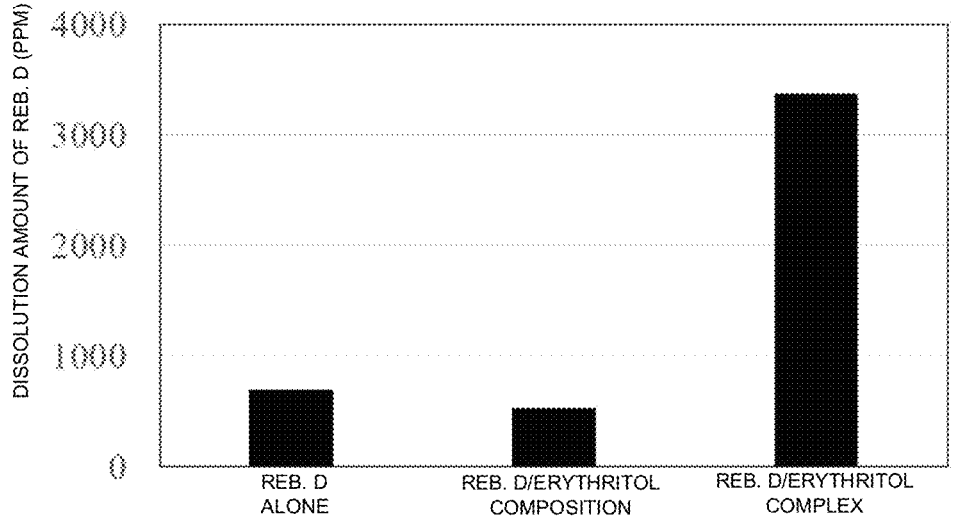
FIG. 4 shows comparison between Reb. D alone, the Reb. D/erythritol composition obtained by simple mixing and the Reb. D/erythritol complex with respect to the solubilities thereof in Example D.

Comparison between the solubilities of Reb. D alone, the Reb. D/erythritol composition obtained by simple mixing and the Reb. D/erythritol complex is shown in FIG. 4.

[Example E] Conformation of Solubility of Complex at Water Temperature of about 25° C.

Figure 5:
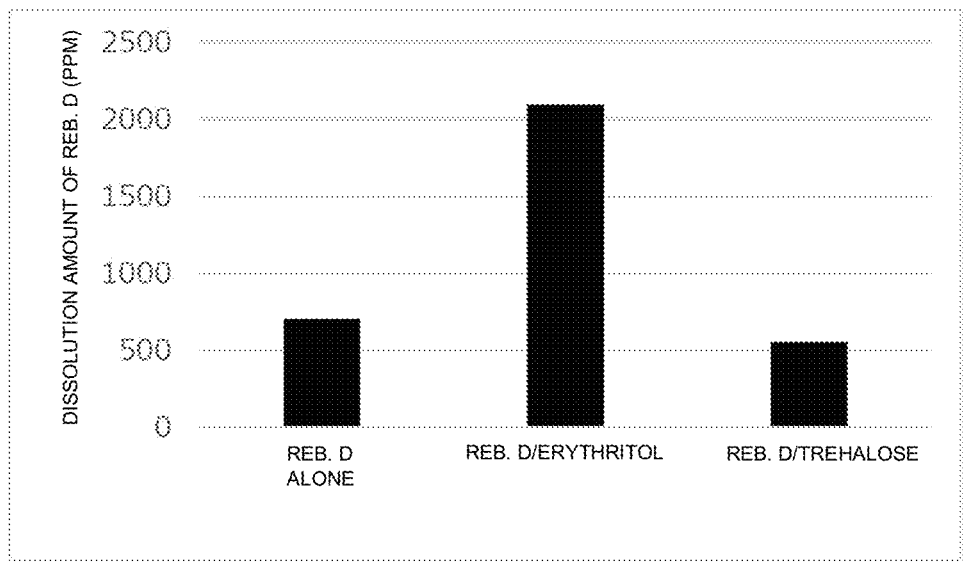
FIG. 5 shows the concentration of Reb. D (dissolution amount of Reb. D) when dissolving each complex obtained in Example E in water.

8 g of erythritol was melted using an oil bath ("OHB-2100" manufactured by TOKYO RIKAKIKAI CO., LTD.) whose temperature was set at 175° C. in advance, and to the obtained melt, 200 mg of the Reb. D formulation was added to be dissolved therein. After that, the melt in which the Reb. D formulation was dissolved was cooled using ice to obtain a Reb. D/erythritol complex. By using a similar procedure, a Reb. D/trehalose complex was obtained. In order to compare the solubilities of samples of these two complexes and Reb. D alone as a control, pure water was added to each sample in a manner such that the concentration of Reb. D in water became 6,666.7 ppm, and stirring was carried out for 30 minutes. The temperatures of a solution containing only Reb. D (Reb. D formulation alone), a solution containing the Reb. D/erythritol complex and a solution containing the Reb. D/trehalose complex were respectively 24.5° C., 23° C. and 24.6° C. After each sample was dissolved, filtration was carried out with a 0.45 μm filter, and then the concentration of Reb. D in a filtrate was measured by LCMS. The results are shown in FIG. 5.

[Example F] Optimization of Melting Temperature

The conditions for preparation of a Reb. D/erythritol complex were changed, and the optimum melting temperature was examined by the below-described procedure.

(1) A composition of 150 mg of the Reb. D formulation (the ratio of Reb. D in TSG: 94.5%) and 4 g of erythritol is produced.
(2) The composition is melted using an oil bath ("OHB-2100" manufactured by TOKYO RIKAKIKAI CO., LTD.) whose temperature is set at each one (140° C., 150° C., 160° C., 170° C., 180° C., 190° C.), and shaking is suitably carried out until complete dissolution is obtained.

(3) The time that elapses before complete dissolution is measured, and then rapid cooling is carried out using ice.

(4) 60 ml of pure water is added to the obtained complex and stirring is carried out for about 10 minutes.

(5) Filtration is carried out with a 0.45 μm filter, and then the ratio of Reb. D in a filtrate is measured by LCMS.

The obtained results are shown in FIG. 6. FIG. 6(A) shows the composition ratio of Reb. D in the solution of the complex obtained at each temperature. Specifically, the ratio of Reb. D in the total steviol glycoside (hereinafter also referred to as "TSG") contained in the complex was examined, and it was confirmed whether or not Reb. D was decomposed. In the temperature zone of 170° C. or higher, significant decomposition of Reb. D was not recognized. FIG. 6(B) shows the time that elapsed before dissolution of Reb. D. The time that elapsed before dissolution of Reb. D was significantly reduced between 160 and 170° C. Reb. D was dissolved in the auxiliary raw material melted using an oil bath whose temperature was set at 170° C., and the dissolution time at that time was changed to obtain a plurality of samples (dissolution times: 5 min, 8 min, 11 min, 14 min, 17 min and 21 min). The ratio of Reb. D in TSG contained in the obtained sample is shown in FIG. 6(C). When the dissolution time was less than 14 minutes, the composition ratio of Reb. D was lower than that of Reb. D before melting, but it was not recognized that significant decomposition of Reb. D occurred.

[Example G] Optimization of Melting Temperature of Reb. D/Rhamnose Complex

Optimization of the melting temperature of the Reb. D/rhamnose complex was examined by a procedure similar to that in Example F, except that erythritol was replaced by rhamnose. The temperatures at which melting was examined were 127° C., 130° C., 132° C., 135° C., 137° C., 140° C., 142° C., 145° C., 147° C., 150° C. and 153° C. The results are shown in FIG. 7. In FIG. 7, "Rhamnose XXX" means a sample dissolved at XXX° C. For example, "Rhamnose 127" means "a sample dissolved at 127° C.". In the temperature zone in the above-described range, significant decomposition of Reb. D was not recognized.

[Example H] Examination of Ratio of Reb. D/Erythritol

Figure 8:
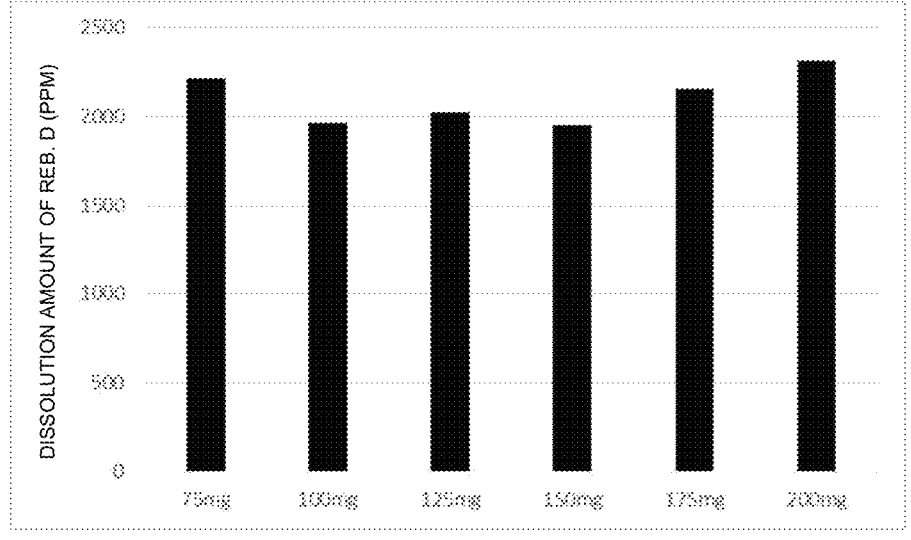
FIG. 8 shows the concentration of Reb. D (dissolution amount of Reb. D) obtained when each complex with each different ratio between Reb. D and erythritol obtained in Example H was dissolved in water in a manner such that the concentration of Reb. D in water became 2,500 ppm, followed by filtration.

The solubility of samples was confirmed in order to determine the suitable addition ratio of Reb. D. 4 g of erythritol was melted using an oil bath ("OHB-2100" manufactured by TOKYO RIKAKIKAI CO., LTD.) whose temperature was set at 180° C., and then 75 mg, 100 mg, 125 mg, 150 mg, 175 mg or 200 mg of the Reb. D formulation was added thereto to be dissolved therein. After cooling on ice, pure water was added to each sample in a manner such that the concentration of Reb. D in water became 2,500 ppm, filtration was carried out with a 0.45 μm filter, and then the concentration of Reb. D in a filtrate was measured by LCMS. The results are shown in FIG. 8.

[Example I] Examination of Ratio of Reb. D/Rhamnose

Figure 9:
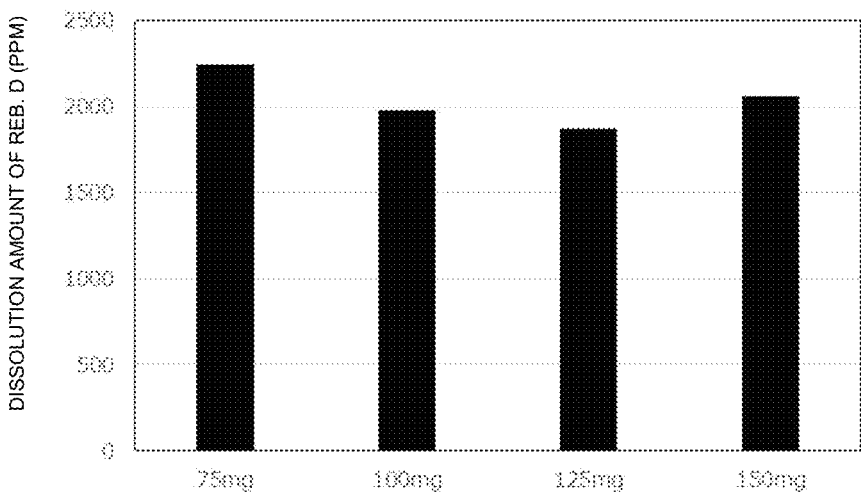
FIG. 9 shows the concentration of Reb. D (dissolution amount of Reb. D) obtained when each complex with each different ratio between Reb. D and rhamnose obtained in Example I was dissolved in water in a manner such that the concentration of Reb. D in water became 2,500 ppm, followed by filtration.

The solubility of samples was confirmed in order to determine the suitable addition ratio of Reb. D. 4 g of rhamnose was melted at 138° C., and then 75 mg, 100 mg, 125 mg or 150 mg of the Reb. D formulation was added thereto to be dissolved therein. After cooling on ice, pure water was added to each sample in a manner such that the concentration of Reb. D in water became 2,500 ppm, filtration was carried out with a 0.45 μm filter, and then the concentration of Reb. D in a filtrate was measured by LCMS. The results are shown in FIG. 9.

[Example J] Evaluation of Flavor

Figure 10:
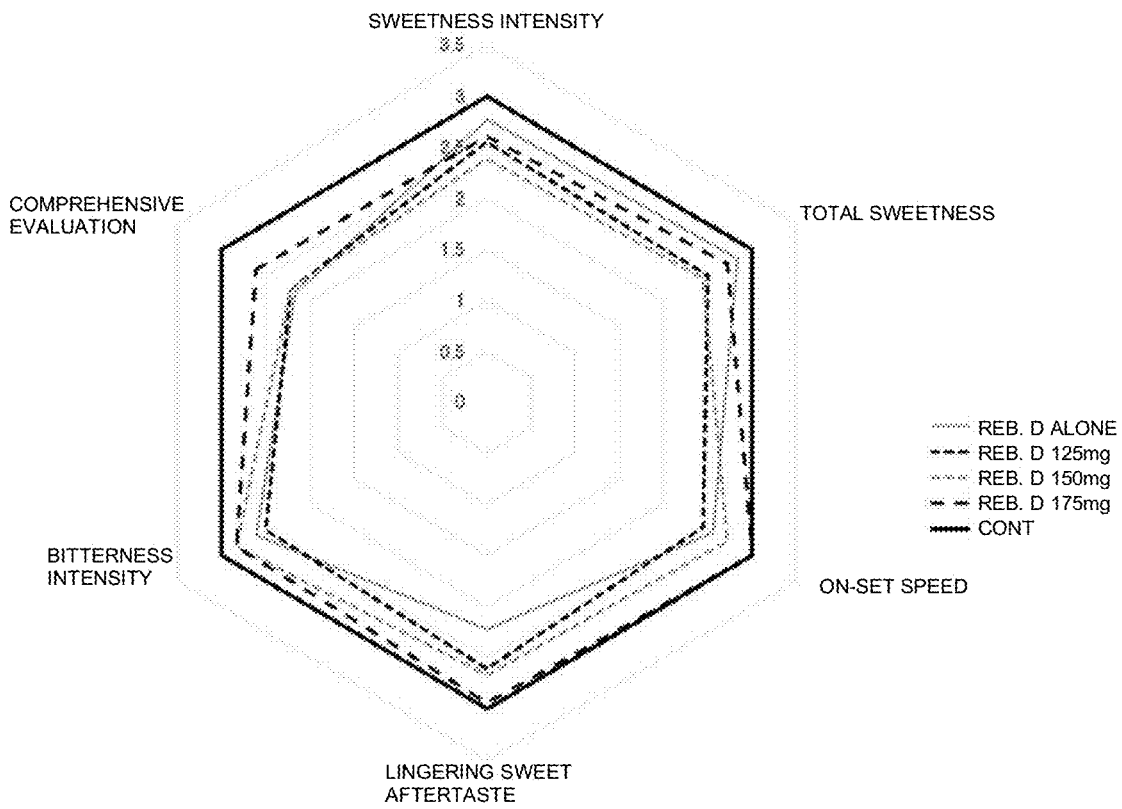
FIG. 10 shows the results of sensory evaluation of each complex with each different ratio between Reb. D and erythritol obtained in Example J.

To 4 g of a melt of erythritol, 125 mg, 150 mg or 175 mg of the Reb. D formulation was added to be dissolved therein, and the mixture was cooled, thereby obtaining a complex sample. It was dissolved in water in a manner such that the sweetness equivalence became 7.5% (that is, the sweetness in terms of sucrose became 7.5%), and evaluation of flavor was made. Evaluation of flavor was made by panelists trained about sensory attributes of sweeteners (7 members) (N=7). The results are shown in FIG. 10. The respective items of evaluation of flavor (sweetness intensity, total sweetness, on-set speed, lingering sweet aftertaste, bitterness intensity and comprehensive evaluation) were scored in increments of 0.5 points in a range of 0 to 6 points. 0 point means low sweetness intensity, small total sweetness, low on-set speed, long lingering sweet aftertaste, high bitterness intensity and poor overall evaluation, and 6 points means high sweetness intensity, large total sweetness, high on-set speed, short lingering sweet aftertaste, low bitterness intensity and satisfactory overall evaluation. As a reference, evaluation with respect to a solution whose sweetness corresponds to the sweetness equivalence of sucrose alone of 7.5% was used as a control (3 points). The comprehensive evaluation of the Reb. D/erythritol complex was equivalent to or higher than that of Reb. D alone. In particular, lingering sweet aftertaste was significantly improved.

[Example K] Influence of Method for Cooling/Solidifying Melt on Solubility of Reb. D In order to examine the influence of the method for cooling and solidifying a melt on the solubility of Reb. D, tests were conducted with experimental standards shown in Table 3. Melting temperature is a set temperature of an oil bath ("OHB-2100" manufactured by TOKYO RIKAKIKAI CO., LTD.). In "Solidification method", in the case of "Rapid cooling at −196° C.", after Reb. D was dissolved, the melt was immersed in liquid nitrogen. In the case of "Room temperature", after heating, the melt was allowed to stand under room temperature environment. In the case of "Stimulation", forced stirring of the melt was carried out under room temperature environment. In the case of "Slow", after heating, the melt was not taken out from the oil bath and was allowed to stand, and after the oil bath was turned off, the melt was slowly cooled to room temperature by the residual heat.

TABLE 3

| Experimental standards | | | | |
| --- | --- | --- | --- | --- |
| Erythritol (g) | Reb.D (mg) | Melting temperature (° C.) | Solidification method | Addition amount of pure water (ml) |
| 4 | 150 | 147 | Rapid cooling at −196° C. | 26.4 |
| 4 | 150 | 147 | Room temperature | 26.4 |

TABLE 3-continued

| Experimental standards | | | | |
|---|---|---|---|---|
| Erythritol (g) | Reb.D (mg) | Melting temperature (° C.) | Solidification method | Addition amount of pure water (ml) |
| 4 | 150 | 147 | Stimulation | 26.4 |
| 4 | 150 | 147 | Slow | 26.4 |

Figure 11:
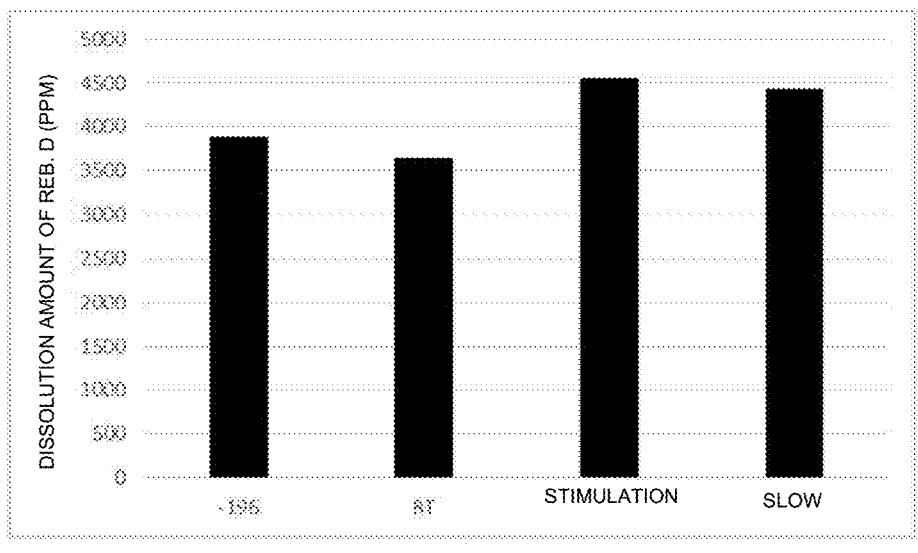
FIG. 11 shows the concentration of Reb. D (dissolution amount of Reb. D) obtained when each complex obtained by changing the method for cooling and solidifying the melt was dissolved in water in Example K.

The concentration of Reb. D dissolved after the addition of pure water is shown in FIG. 11. In the drawing, "−196" means "a sample rapidly cooled at −196° C.". The dissolution amount of Reb. D was improved with respect to all the standards, but among the samples tested this time, the sample solidified by "Stimulation" and the sample solidified by "Slow" showed larger dissolution amounts.

[Example L] Examination of Addition Order of Raw Materials

In order to examine the relationship between the addition order of raw materials at the time of melting for obtaining a Reb. D/erythritol complex and the solubility of the complex obtained thereby, the addition order of raw materials was changed to prepare complexes. The addition conditions are as described below.

Condition A: Using an oil bath ("OHB-2100" manufactured by TOKYO RIKAKIKAI CO., LTD.), 100 mg of the Reb. D formulation was allowed to stand to be subjected to heat treatment at 100° C. for 1.5 H, and it was added to erythritol that was melted in advance.

Condition B: 4 g of erythritol was melted using an oil bath whose temperature was set at 145° C. in advance, and 100 mg of the Reb. D formulation which was not subjected to heat treatment was added thereto.

Condition C: 100 mg of the Reb. D formulation was mixed with 4 g of erythritol at room temperature, and the obtained mixture was heated to 145° C. using an oil bath to prepare a melt.

In each of Conditions A to C, cooling after the dissolution of Reb. D was carried out by rapid cooling on ice. The complex obtained by each of Conditions A to C was dissolved in water at room temperature, and the water solubility thereof was confirmed. The results are shown in FIG. 12(A) and Table 4.

TABLE 4

| | Time that elapsed before complete dissolution (min)* | Heating temperature (° C.) | Addition amount of water (ml) (Adjusted in a manner such that the concentration of Reb. D became 2000 ppm) | Time that elapsed before dissolution in water (min) |
|---|---|---|---|---|
| Cond. A | 6.5 | 145 | 50 | 4.3 |
| Cond. B | 9.5 | 145 | 50 | 5.9 |
| Cond. C | 10.9 | 145 | 50 | 7 |

*It means the time that elapsed from the start of dissolution of Reb. D in erythritol.

Further, comparison between Conditions A to C was made with respect to the ratios of Reb. D and Reb. B to the total steviol glycoside (TSG). It is shown in FIG. 12(B).

From the results, it was found that the dissolution time from the addition of the Reb. D formulation is more shortened and the decomposition is less likely to occur in the case where the Reb. D formulation is added after the melt of erythritol is prepared when compared to the case where the Reb. D formulation is mixed with erythritol in advance. Further, it was found that when the Reb. D formulation is heated at about 100° C. in advance before it is added to the melt, the time that elapses before complete dissolution is further reduced and the time that elapses before dissolution in water is also shortened.

Figure 13:
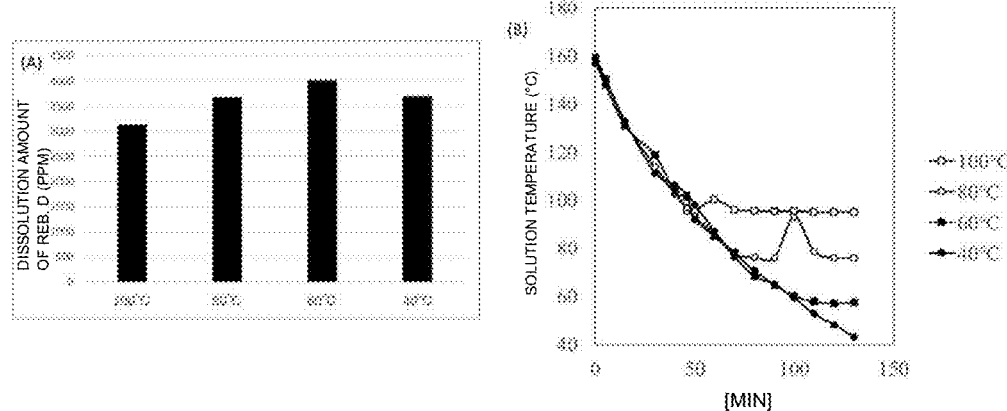
FIG. 13 shows the test results of each complex obtained by changing the solidification temperature in Example M.

[Example M] Examination of Influence of Solidification Temperature on Solubility After a solution of erythritol (4 g)/Reb. D formulation (150 mg) was prepared at 165° C., a heat-resistant container containing the solution was immersed in a thermostatic bath whose temperature was set at each of various temperatures (40° C., 60° C., 80° C., 100° C.) in advance and cooled. The temperature change of each sample at the time of cooling is shown in FIG. 13(B). Further, the temperature transition and the average cooling rate for 130 minutes from the start of cooling are shown in the table below. "Cooling rate (° C./min)" indicates an average cooling rate at each time point. For example, regarding the cooling rate at the time point of 25 min, the temperature reduced in 25 minutes from the temperature at the time point of 0 min (in the case of cooling at 100° C., 158.9° C.–106.7° C.=52.2° C.) is divided by the time (25 min) to obtain the average cooling rate (2.09° C./min).

TABLE 5

| Temperature transition and average cooling rate for 130 minutes from start of cooling | | | | | | | | | | | | | | | |
|---|---|---|---|---|---|---|---|---|---|---|---|---|---|---|---|
| | 0 min | 5 min | 15 min | 30 min | 40 min | 46 min | 50 min | 60 min | 70 min | 80 min | 90 min | 100 min | 110 min | 120 min | 130 min |
| Temperature transition (° C.) | | | | | | | | | | | | | | | |
| 100° C. | 158 | 150.3 | — | 118.5 | — | 95.7 | 95.5 | 100.2 | 96.2 | 95.7 | 95.3 | 95.5 | 95 | 95 | 95 |
| 80° C. | 158 | 150.6 | 132.3 | 113.8 | 102.5 | 96.9 | 93.3 | 85.8 | 77.7 | 76.2 | 76.1 | 93 | 78.7 | 76.1 | 76.1 |
| 60° C. | 157.2 | 147.9 | 131 | 118.7 | 103.3 | 101.2 | 92 | 85 | 78 | 70.5 | 64.9 | 60.1 | 57.7 | 57.1 | 57.5 |
| 40° C. | 159.5 | 150.5 | 132.7 | 111.3 | 106.4 | 102.2 | 98.2 | 86.9 | 76.5 | 68.2 | 65.2 | 59.3 | 52.8 | 48.2 | 43.3 |
| Cooling rate (° C./min) (average) | | | | | | | | | | | | | | | |
| 100° C. | — | 1.54 | — | 1.32 | — | 1.35 | 1.25 | 0.96 | 0.88 | 0.78 | 0.70 | 0.63 | 0.57 | 0.53 | 0.48 |
| 80° C. | — | 1.48 | 1.71 | 1.47 | 1.39 | 1.33 | 1.29 | 1.20 | 1.15 | 1.02 | 0.91 | 0.65 | 0.72 | 0.68 | 0.63 |
| 60° C. | — | 1.86 | 1.75 | 1.28 | 1.35 | 1.22 | 1.30 | 1.20 | 1.13 | 1.08 | 1.03 | 0.97 | 0.90 | 0.83 | 0.77 |
| 40° C. | — | 1.80 | 1.79 | 1.61 | 1.33 | 1.25 | 1.23 | 1.21 | 1.19 | 1.14 | 1.05 | 1.00 | 0.97 | 0.93 | 0.89 |

After a Reb. D/erythritol complex was formed, 53 g of pure water was added to each sample, and after the complex was dissolved, filtration was carried out, and the concentration of Reb. D contained in a filtrate was measured. The results are shown in FIG. 13(A). In particular, the samples cooled in the thermostatic bath at a temperature of 60° C. to 80° C. gave large dissolution amounts of Reb. D.

[Example N] Examination of Temperature at the Time of Solidification and Crystal Form Obtained After a solution of erythritol (8 g)/Reb. D formulation (300 mg) was prepared at 170° C., a heat-resistant container containing the solution was immersed in a thermostatic bath whose temperature was set at each of various temperatures Temperature history D: The sample was rapidly cooled to 70° C. using ice in the early stage of cooling, and then natural cooling was carried out at normal temperature.

Figure 15:
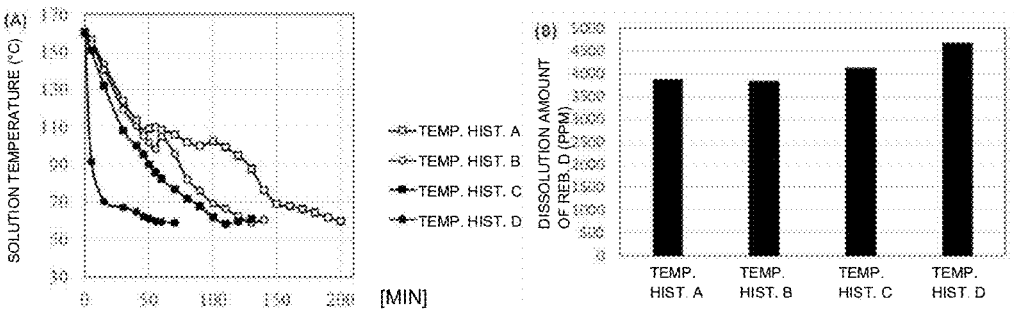
FIG. 15 shows the test results of each complex obtained by changing the cooling rate at the time of solidification in Example O.

The results are shown in FIG. 15(A). Further, the temperature transition and the average cooling rate for 60 minutes from the start of cooling are shown in the table below. "Cooling rate (° C./min)" indicates an average cooling rate at each time point. For example, regarding the cooling rate at the time point of 30 min, the temperature reduced in 30 minutes from the temperature at the time point of 0 min (in the case of Temperature history A, 160.9° C.−124.1° C.=36.8° C.) is divided by the time (30 min) to obtain the average cooling rate (1.23° C./min).

TABLE 6

| Temperature transition and average cooling rate for 180 minutes from start of cooling | | | | | | | | | | | |
| --- | --- | --- | --- | --- | --- | --- | --- | --- | --- | --- | --- |
| | 0 min | 5 min | 15 min | 30 min | 40 min | 46 min | 50 min | 55 min | 60 min | 70 min | 80 min |
| Temperature transition (° C.) | | | | | | | | | | | |
| History A | 160.9 | 156.5 | 143.4 | 124.1 | 113.5 | 107.5 | 109.4 | 109.9 | 108.7 | 106 | 102 |
| History B | 160.8 | 154.5 | 140.8 | 119.5 | 110.7 | 105.5 | 101.9 | 98.2 | 105.1 | 95.8 | 82.2 |
| History C | 160.1 | 150.8 | 132 | 108.1 | 100.1 | 95.5 | 90.1 | 86.1 | 82.4 | 76.9 | 71.8 |
| History D | 160.5 | 91.6 | 70.5 | 67.3 | 64.8 | 62.3 | 61.1 | 59.8 | 59.4 | 59 | |
| Cooling rate (° C./min) (average) | | | | | | | | | | | |
| History A | — | 0.88 | 1.17 | 1.23 | 1.19 | 1.16 | 1.03 | 0.93 | 0.87 | 0.78 | 0.74 |
| History B | — | 1.26 | 1.33 | 1.38 | 1.25 | 1.20 | 1.18 | 1.14 | 0.93 | 0.93 | 0.98 |
| History C | — | 1.86 | 1.87 | 1.73 | 1.50 | 1.40 | 1.40 | 1.35 | 1.30 | 1.19 | 1.10 |
| History D | — | 13.78 | 6.00 | 3.11 | 2.39 | 2.13 | 1.99 | 1.83 | 1.69 | 1.45 | |

| | 90 min | 100 min | 110 min | 120 min | 130 min | 140 min | 150 min | 160 min | 170 min | 180 min |
| --- | --- | --- | --- | --- | --- | --- | --- | --- | --- | --- |
| Temperature transition (° C.) | | | | | | | | | | |
| History A | 100 | 102.4 | 99.3 | 94.8 | 87.8 | 76.4 | 69.1 | 68 | 66.3 | 64.4 |
| History B | 76 | 69.5 | 66.4 | 62.7 | 59.1 | 60.6 | | | | |
| History C | 67.8 | 61.9 | 58.4 | 60 | 60.9 | | | | | |
| History D | | | | | | | | | | |
| Cooling rate (° C./min) (average) | | | | | | | | | | |
| History A | 0.68 | 0.59 | 0.56 | 0.55 | 0.56 | 0.60 | 0.61 | 0.58 | 0.56 | 0.54 |
| History B | 0.94 | 0.91 | 0.86 | 0.82 | 0.78 | 0.72 | | | | |
| History C | 1.03 | 0.98 | 0.92 | 0.83 | 0.76 | | | | | |
| History D | | | | | | | | | | |

Figure 14:
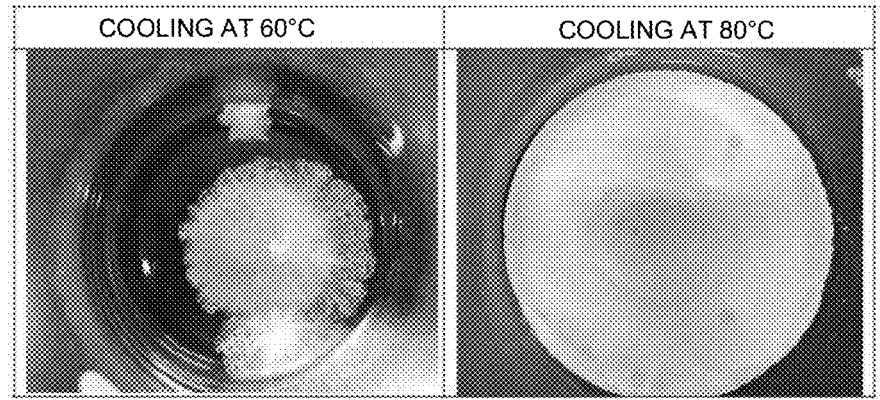
FIG. 14 shows photographs of the crystals obtained in Example N.

(25° C., 60° C., 80° C.) in advance and cooled. Photographs of the crystals obtained at the respective temperatures are shown in FIG. 14.

[Example O] Examination of Influence of Solidification Rate on Solubility

After a solution of erythritol (4 g)/Reb. D formulation (150 mg) was prepared at 165° C., it was cooled to 60° C. while controlling the cooling temperature. Classification into temperature histories A to D was made according to the difference in the cooling rate. The details thereof are as described below. As an oil bath, "OHB-2100" manufactured by TOKYO RIKAKIKAI CO., LTD. was used.

Temperature history A: The temperature of the oil bath was adjusted to about 100° C. 100 minutes later, the oil bath was turned off, and the sample was naturally cooled to 60° C.

Temperature history B: The oil bath was turned off, and the sample was naturally cooled.

Temperature history C: The oil bath was turned off, and oil at room temperature was added to carry out cooling faster than natural cooling.

After a Reb. D/erythritol complex was formed, 53 g of pure water was added to each sample, and after the complex was dissolved, filtration was carried out, and the concentration of Reb. D contained in a filtrate was measured. The results are shown in FIG. 15(B).

Figure 16:
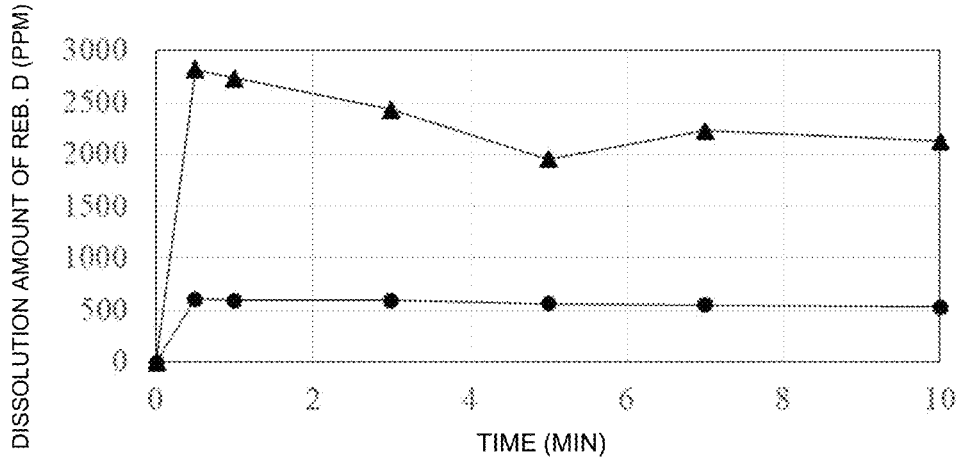
FIG. 16 shows comparison between the Reb. D/erythritol complex and the Reb. D formulation with respect to the dissolution amount and the dissolution rate in Example P.

[Example P] Comparison with Reb. D Formulation with Respect to Dissolution Amount and Dissolution Rate Under the conditions described in Table 7, a Reb. D/erythritol complex was prepared. After the complex was weighed, it was powdered using a mortar. After that, under the conditions described in Table 8, pure water was added, and sampling was carried out over time while stirring to confirm dissolution behavior of Reb. D. As a control, the Reb. D formulation was subjected to a similar experiment. The results are shown in FIG. 16.

TABLE 7

| Conditions for preparation of Reb. D/erythritol complex | | | | | | | |
|---|---|---|---|---|---|---|---|
| Erythritol (g) | Reb. D (mg) | Total (g) | Ratio of Reb. D (%) | Temperature of melt (Setting) | Temperature of melt (Measured) | Dissolution time of melt (min) | Final temperature for solidification (° C.) |
| 8 | 200 | 8.20 | 2.44% | 190 | 177 | 1 | Room temperature |

TABLE 8

| Dissolution conditions | | | | |
|---|---|---|---|---|
| Complex (g) | Amount of Reb. D (mg) | Aimed dissolution amount (ppm) | Addition amount of water (ml) | Stirring speed (rpm) |
| 3.4 | 74.63 | 4000 | 18.7 | 150 |

Example Q

In this example, a Reb. D formulation (purity: 95% (w/w), manufactured by Jining Renewal and Joint International), erythritol (purity: 98% (w/w) or more, manufactured by Mitsubishi-Chemical Foods Corporation) and fructose (purity: 95% (w/w) or more, manufactured by NACALAI TESQUE, INC.) were used. The concentration of Reb. D contained in a filtrate was analyzed using a liquid chromatograph mass spectrometer (LCMS) ("LCMS 8050" manufactured by Shimadzu Corporation).

A two-component complex of erythritol/Reb. D was prepared by the below-described procedure. Firstly, 4 g of erythritol was melted in an oil bath whose temperature was set at 175° C. or higher to obtain a solvent, and 100 mg of Reb. D was added to the solvent, and then stirring was carried out for 2 minutes. The solvent in which Reb. D was dissolved was transferred to a preheated oil bath (60° C.). A three-component complex of erythritol/Reb. D/fructose was prepared as described below. In a manner similar to that for the preparation of the two-component complex, 100 mg of Reb. D was dissolved in 3.2 g of erythritol and complete dissolution was visually confirmed. 1.5 minutes after that, 0.8 g of fructose was added thereto, thereby preparing the three-component complex. After stirring for 0.5 minute, a glass vial containing the melted complex was transferred to a preheated oil bath (60° C.). The melted complex was solidified to obtain a complex (containing 2.4% w/w of Reb. D) and it was used for evaluation.

(Evaluation of Solubility)
Measurement of Dissolution Amount of Reb. D in Water

Figure 17:
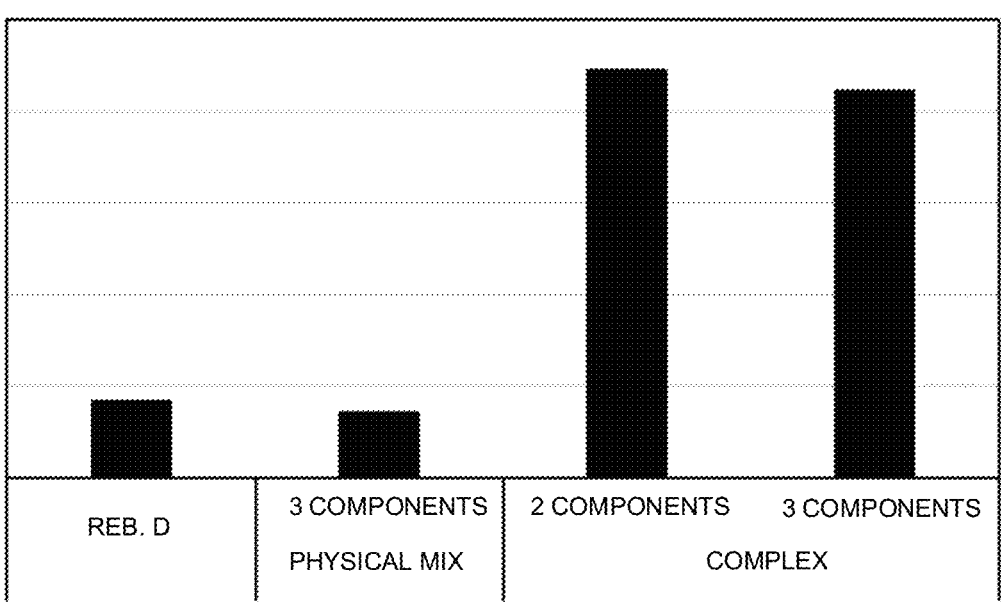
FIG. 17 shows the results of the measurement of the dissolution amount of Reb. D in water in Example Q.

A material consisting of only Reb. D (Reb. D alone), a composition obtained by simply mixing erythritol, Reb. D formulation and fructose (Physical mix), and the two-component complex and three-component complex prepared by melting as described above were respectively powdered, and each one was added to water at room temperature and subjected to adjustment in a manner such that the concentration of Reb. D became about 4,000 mg/L. The room temperatures at the time of preparing samples of Reb. D alone, Physical mix, the two-component complex and the three-component complex were respectively 21.6° C., 20.0° C., 21.9° C. and 17.6° C. After stirring for 5 minutes, each sample was filtered with a membrane filter (0.45 μm PTFE membrane filter, manufactured by TOSC Japan Ltd.). The concentration of Reb. D in each filtrate was measured by LCMS. The results are shown in FIG. 17.

Examination of Dissolution Rate of Erythritol/Reb. D/Fructose Complex

Figure 18:
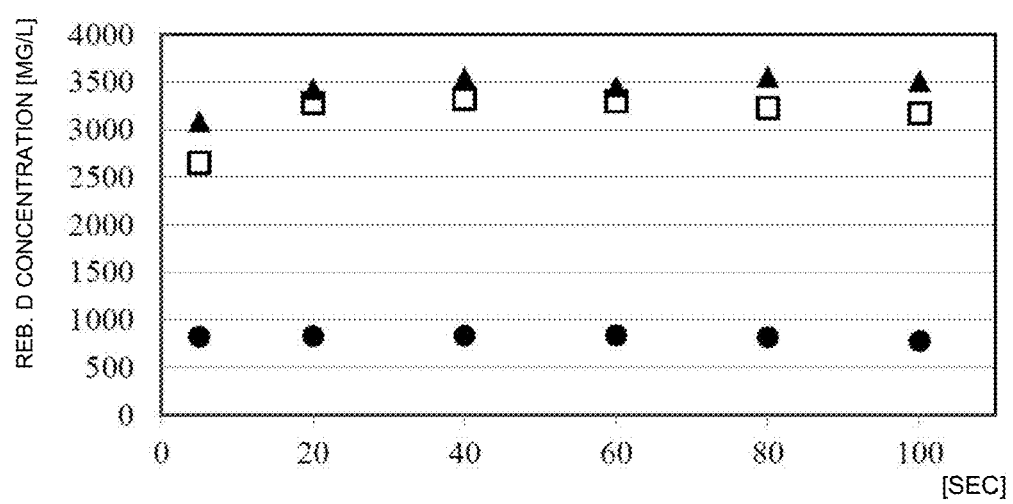
FIG. 18 shows the examination results of the dissolution rate of the erythritol/Reb. D/fructose complex in Example Q.

Each of the two-component complex and the three-component complex prepared as described above was added to water and subjected to adjustment in a manner such that the concentration of Reb. D became about 4,000 mg/L, and then the mixture was stirred at room temperature at 150 rpm. As a control, Reb. D alone was also dissolved by a similar procedure. After a predetermined amount of time passed from the start of stirring, a part of each sample was collected and filtered with a 0.45 μm PTFE membrane filter. The concentration of Reb. D in each filtrate was measured by LCMS. The results are shown in FIG. 18.

Evaluation of Flavor

Figure 19:
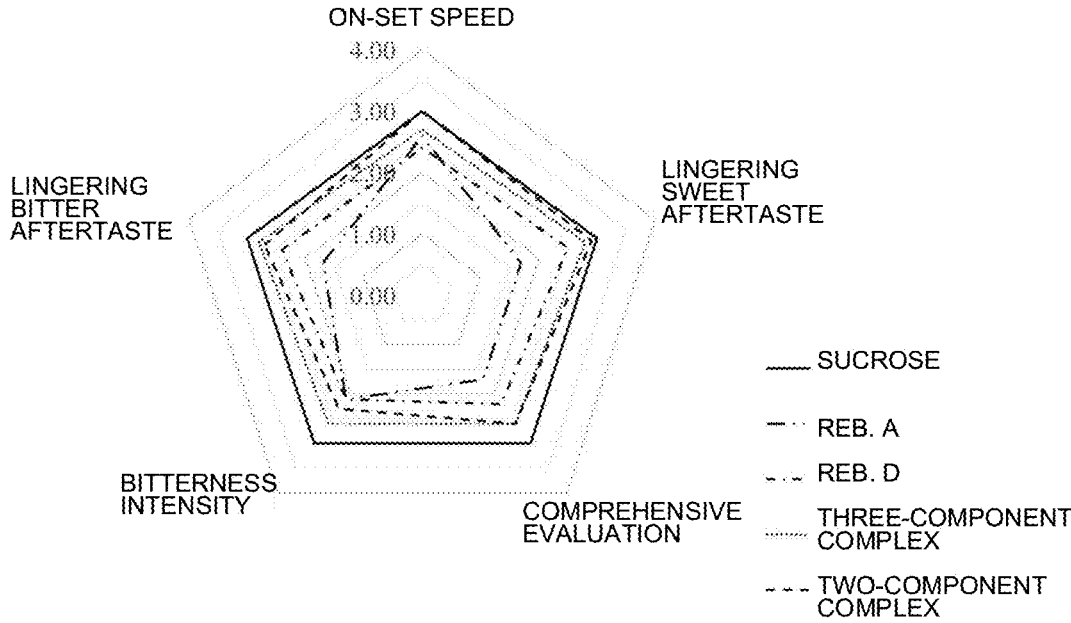
FIG. 19 shows the results of evaluation of flavor in Example Q.

In order to confirm effects of the three-component complex of erythritol/Reb. D/fructose, evaluation of flavor was made. Reb. A and Reb. D were also used, and sucrose was used as a control. Each of a two-component complex and a three-component complex was prepared as a solid according to the method of the working example so that about 3.6% of Reb. D was contained. Each of the complexes or Reb. A was subjected to adjustment by adding water thereto in a manner such that the amount in terms of Reb. A or Reb. D became 300 mg/L. The concentration of the sucrose solution was adjusted to be 9 SEV (sucrose equivalent value). Evaluation of taste quality was made by panelists trained about sensory attributes of sweeteners (5 members). The respective items of evaluation of flavor (on-set speed, lingering sweet aftertaste, bitterness intensity, lingering bitter aftertaste and comprehensive evaluation) were scored in a range of 0 to 6 points. As a reference, sucrose alone was used as a control (3 points). 6 points means high on-set speed of sweetness, short lingering sweet aftertaste, low bitterness intensity, short lingering bitter aftertaste and satisfactory overall evaluation. The results are shown in Table 9 and FIG. 19.

TABLE 9

| | Sucrose | Reb. A | Reb. D | Three-component complex | Two-component complex |
|---|---|---|---|---|---|
| On-set speed | 3.00 | 2.60 | 2.40 | 2.70 | 3.00 |
| Lingering sweet aftertaste | 3.00 | 1.70 | 2.50 | 2.80 | 2.90 |
| Comprehensive evaluation | 3.00 | 1.70 | 2.20 | 2.60 | 2.60 |
| Bitterness intensity | 3.00 | 2.10 | 2.10 | 2.60 | 2.30 |
| Lingering bitter aftertaste | 3.00 | 1.70 | 2.40 | 2.80 | 2.70 |

SEM Photographs

Figure 20:
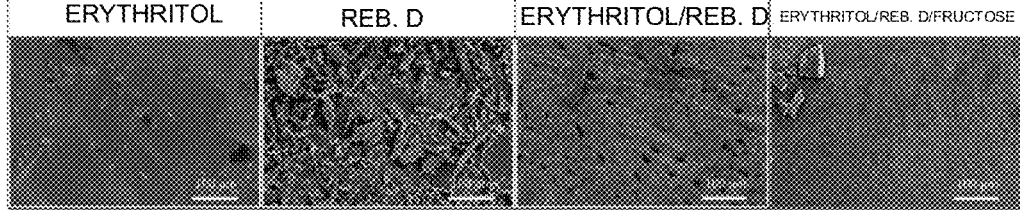
FIG. 20 shows electron microscope photographs of the samples in Example Q.

The surface structure of the complex was observed using a scanning electron microscope (SEM). Each of samples (erythritol alone, Reb. D alone, a two-component complex of erythritol and Reb. D, and a three-component complex of erythritol, Reb. D and fructose) was attached to a conductive double-sided tape, and it was fixed to a mount of a microscope. The dried sample was covered with gold to reduce the charge effect. The test was conducted at an acceleration voltage of 10 kV using a JSM-6510 microscope (manufactured by JEOL Ltd.). Regarding erythritol, it was temporarily melted at 175° C. and then solidified, and after that, the solid surface was observed. The results are shown in FIG. 20. It was recognized that the gaps in the solid surface of the two-component complex are larger than those of the three-component complex when observing the outer appearances thereof.

The invention claimed is:

1. A complex comprising:

Reb. D; and erythritol wherein the water solubility of Reb. D at a water temperature of 25° C. is 75 to 700 mg/100 g-$H_2O$, wherein the complex excludes a complex obtained by a spray drying method, and wherein the complex has a peak at at least one selected from 2θ=14.8±0.2 deg, 20.2±0.2 deg, 24.5±0.2 deg and 27.9±0.2 deg in X-ray diffraction (CuKα: λ=1.5405 Å).

2. The complex according to claim 1, wherein the complex comprises a eutectic crystal.

3. The complex according to claim 1, wherein the content of Reb. D is an amount equal to or less than the saturation solubility relative to the erythritol.

4. The complex according to claim 1, wherein the content of Reb. D is 10 to 300 mg relative to 1 g of erythritol.

5. The complex according to claim 1, wherein the complex further comprises fructose, and wherein the content of Reb. D is 10 to 300 mg relative to 1 g of the total of the erythritol and fructose.

6. A sweetener composition comprising the complex according to claim 1.

7. The sweetener composition according to claim 6, further comprising at least one selected from the group consisting of Reb. A, Reb. B, Reb. C, Reb. E, Reb. F, Reb. G, Reb. I, Reb. J, Reb. K, Reb. M, Reb. N, Reb. O, Reb. Q, Reb. R, Reb. V, Reb. W, Reb. KA, dulcoside A, rubusoside, steviol, steviolmonoside, steviolbioside, stevioside, sucrose, high fructose corn syrup, erythritol, Mogroside V, corn syrup, aspartame, sucralose, acesulfame potassium, saccharin and xylitol.

8. A food or beverage comprising the complex according to claim 1.

9. The complex according to claim 1, wherein the complex further comprises at least one carbohydrate other than erythritol.

10. The complex according to claim 9, wherein the content of Reb. D is 10 to 300 mg relative to 1 g of the erythritol and the at least one carbohydrate other than erythritol.

* * * * *